United States Patent [19]

Sunagawa et al.

[11] Patent Number: 5,093,328
[45] Date of Patent: * Mar. 3, 1992

[54] BETA-LACTAM COMPOUNDS

[75] Inventors: Makoto Sunagawa; Haruki Matsumura; Takaaki Inoue; Masatomo Fukasawa; Masuhiro Kato, all of Osaka, Japan

[73] Assignee: Sumitomo Pharmaceuticals Company, Limited, Osaka, Japan

[*] Notice: The portion of the term of this patent subsequent to Jul. 24, 2007 has been disclaimed.

[21] Appl. No.: 30,496

[22] Filed: Mar. 27, 1987

[30] Foreign Application Priority Data

Mar. 27, 1986 [JP] Japan .................. 61-67160
Mar. 31, 1986 [JP] Japan .................. 61-71034
May 6, 1986 [JP] Japan .................. 61-101977

[51] Int. Cl.$^5$ .................. C07D 487/04; A61K 31/40
[52] U.S. Cl. .................. 514/210; 540/350
[58] Field of Search .................. 540/350; 514/210

[56] References Cited

U.S. PATENT DOCUMENTS 4,943,569  7/1990  Sunagawa et al. .................. 540/310
4,962,103 10/1990  Sunagawa et al. .................. 514/210

FOREIGN PATENT DOCUMENTS 0072710  8/1982  European Pat. Off. .
0126587 11/1984  European Pat. Off. .
0182213 11/1985  European Pat. Off. .
0238285  3/1987  European Pat. Off. .
59-16892  1/1984  Japan .

OTHER PUBLICATIONS

Heterocycles, vol. 21, No. 1 (1984), pp. 29–40.
Journal of Antibiotics, 36, vol. 8, pp. 1034–1039 (1983).
Abstract of the 4th Symposium on Medicinal Chemistry sponsored by Pharmaceutical Society of Japan (1982).

*Primary Examiner*—Nicholas S. Rizzo
*Attorney, Agent, or Firm*—Birch, Stewart, Kolasch & Birch

[57] ABSTRACT

A beta-lactam compound of the formula:

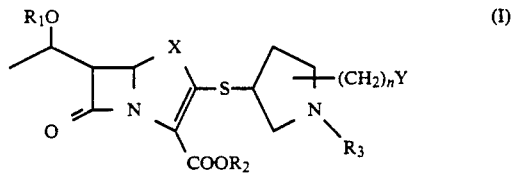

or a pharmaceutically acceptable salt thereof, which is useful as an anti-microbial agent or an intermediate in the synthesis of anti-microbial agents.

28 Claims, No Drawings

BETA-LACTAM COMPOUNDS

The present invention relates to beta-lactam compounds, and their production. More specifically, the invention relates to novel beta-lactam compounds which belong to the carbapenem (i.e. 1-azabicyclo[3.2.0]hept-2-en-7-one-2-carboxylic acid) system or the penem (i.e. 1-azabicyclo-[3.2.0]hept-2-en-7-one-4-thia-2-carboxylic acid) system and which are useful as anti-microbial agents or intermediates in the synthesis of anti-microbial agents, and their production.

The beta-lactam compounds of this invention are representable by the formula:

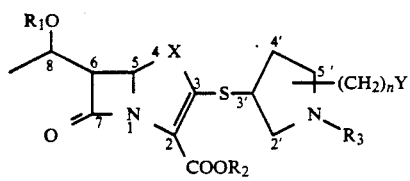

(I)

wherein $R_1$ is a hydrogen atom or a protective group for hydroxyl; $R_2$ is a hydrogen atom or a protective group for carboxyl; X is a methylene group optionally substituted with lower alkyl or a sulfur atom; $R_3$ is a lower alkyl group when X is a methylene group optionally substituted with lower alkyl, or a hydrogen atom, a lower alkyl group or a protective group for amino when X is a sulfur atom; Y is either one of the following formulas:

$$\underset{\underset{R_5}{}}{-\overset{O}{\overset{\|}{C}}-N\diagup^{R_4}}$$ (1)

(in which $R_4$ and $R_5$ are, the same or different, each a hydrogen atom or a lower alkyl group, or they are combined together to represent an alkylene group having 2 to 6 carbon atoms), $$-ZCOR_6$$ (2)

(in which Z is an imino group (—NH—) or an oxygen atom (—O—) and $R_6$ is an amino group optionally substituted with lower alkyl, a lower alkoxy group or a lower alkyl group), $$\underset{H}{-N-\overset{\overset{R_7}{|}}{C}=NH}$$ (3)

(wherein $R_7$ is a hydrogen atom or a lower alkyl group), $$-CH=N-R_8$$ (4)

(wherein $R_8$ is an amino group substituted with lower alkyl or a lower alkoxy group) and $$-CO-N-N\diagdown\underset{R_{10}}{\overset{R_{11}}{|}}\diagup^{}$$ (5)

(wherein $R_9$, $R_{10}$ and $R_{11}$ are, the same or different, each a hydrogen atom or a lower alkyl group), or an optionally protected amino group, a carboxyl group, a lower alkoxycarbonyl group, an ar(lower)alkyloxycarbonyl group, a cyano group, a hydroxyl group, a lower alkoxy group, a lower alkylthio group or a lower alkanesulfonyl group; and n is an integer of 0 to 4, provided that when $R_3$ represents a hydrogen atom or a protective group for amino, n is an integer of 1 to 4. Not only these beta-lactam compounds (I) but also their pharmaceutically acceptable salts are included within the scope of this invention.

Since the successful isolation of an anti-microbial substance "thienamycin" from the nature [U.S. Pat. No. 3,950,357; J.Am.Chem.Soc., 100, 313 (1978)], the synthesis of various carbapenem and penem compounds have been developed.

As a result of an extensive study, it has now been found that the beta-lactam compounds (I), which are characteristic in having a substituent readily derivable from 4-hydroxyproline as a side chain at the 2-position of the carbapenem or penem skeleton, exhibit a strong anti-microbial activity and are valuable as anti-microbial agents or intermediates for the production of anti-microbial agents.

Throughout this specification, particularly in the above formula (I), the term "lower" is generally intended to mean any group having not more than 8 carbon atoms, particularly not more than 5 carbon atoms, more particularly not more than 3 carbon atoms. Specific examples of the lower alkyl group are methyl, ethyl, n-propyl, isopropyl, n-butyl, sec-butyl, t-butyl, n-pentyl, etc. Examples of lower alkoxy are methoxy, ethoxy, n-propoxy, isopropoxy, n-butoxy, secbutoxy, t-butoxy, n-pentoxy, etc. Examples of lower alkylthio are methylthio, ethylthio, n-propylthio, isopropylthio, n-butylthio, sec-butylthio, t-butylthio, n-pentylthio, etc. Examples of lower alkanesulfonyl are methanesulfonyl, ethanesulfonyl, etc.

The term "ar" is intended to mean a carbocyclic aromatic hydrocarbon group having usually not more than 18 carbon atoms, particularly not more than 10 carbon atoms, which may be substituted with lower alkyl, lower alkoxy, nitro, etc. Specific examples are phenyl, p-methoxyphenyl, o-nitrophenyl, p-nitrophenyl, naphthyl, etc.

When $R_4$ and $R_5$ are combined together to represent an alkylene group having 2 to 6 carbon atoms, the group of the formula:

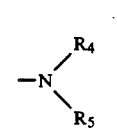

is a 3- to 7-membered nitrogen-containing heterocyclic group such as aziridino, azetidino, pyrrolidino or piperazino. The amino group substituted with lower alkyl, which is represented by $R_6$ or $R_8$ may be methylamino, ethylamino, dimethylamino, diethylamino or the like.

General protection of the functional groups such as hydroxyl, carboxyl and amino are disclosed in various textbooks such as "Protective Groups in Organic Synthesis" (1981) published by John Wiley & Sons, New York, U.S.A. and "New Experimental Chemistry" ("Shin-Jikken Kagaku Koza" in Japanese), Vol. 14 (1978) published by Maruzen, Tokyo, Japan as well as many literature references as cited in those textbooks.

Conventional protecting groups as disclosed therein are ordinarily usable in this invention.

Specific examples of the protecting group for hydroxyl are a lower alkyl group such as a $C_1$–$C_4$ alkyl (e.g. methyl, ethyl, n-propyl, isopropyl, n-butyl, sec-butyl, t-butyl), a substituted methyl group (e.g. methoxymethyl, benzyloxymethyl, 2-methoxyethoxymethyl, t-butoxymethyl, methylthiomethyl, 2,2,2-trichloroethoxymethyl), a tetrahydropyranyl group, a substituted ethyl group (e.g. 1-ethoxyethyl, 1-methyl-1-methoxyethyl, trichloroethyl), an optionally substituted monophenylmethyl, diphenylmethyl or triphenylmethyl group (e.g. benzyl, p-methoxybenzyl, o-nitrobenzyl, p-nitrobenzyl, p-chlorobenzyl, diphenylmethyl, triphenylmethyl), a substituted silyl group (e.g. trimethylsilyl, triethylsilyl, t-butyldimethylsilyl, t-butyldiphenylsilyl), a formyl group, a lower alkanoyl group such as a $C_2$–$C_5$ alkanoyl (e.g. acetyl, isobutyroyl, pivaloyl), a halogenated lower alkanoyl group (e.g. dichloroacetyl, trichloroacetyl, trifluoroacetyl), an arylcarbonyl group (e.g. benzoyl, toluoyl, naphthoyl), a lower alkoxycarbonyl group such as a $C_1$–$C_5$ alkoxycarbonyl (e.g. methoxycarbonyl, ethoxycarbonyl, isobutoxycarbonyl), a halogenated lower alkoxycarbonyl group such as a $C_1$–$C_5$ alkoxycarbonyl substituted with one to three halogen atoms (e.g. 2-iodoethoxycarbonyl, 2,2,2-trichloroethoxycarbonyl), a lower alkenyloxycarbonyl group such as $C_2$–$C_6$ alkenyloxycarbonyl (e.g. vinyloxycarbonyl, allyloxycarbonyl), an optionally substituted arylmethyloxycarbonyl group such as an optionally substituted phenylmethyloxycarbonyl (e.g. benzyloxycarbonyl, p-methoxybenzyloxycarbonyl, 2,4-dimethoxybenzyloxycartonyl, o-nitrobenzyloxycarbonyl, p-nitrobenzyloxycarbonyl), etc.

Specific examples of the protecting group for carboxyl are a lower alkyl group such as a $C_1$–$C_4$ alkyl (e.g. methyl, ethyl, n-propyl, isopropyl, n-butyl, sec-butyl, t-butyl), a halogenated lower alkyl group such as $C_1$–$C_4$ alkyl substituted with one to three halogen atoms (e.g. 2-iodoethyl, 2,2,2-trichloroethyl), a lower alkoxymethyl group such as $C_1$–$C_4$ alkoxymethyl (e.g. methoxymethyl, ethoxymethyl, isobutoxymethyl), a lower alkoxycarbonyloxyethyl group such as $C_1$–$C_4$ alkoxycarbonyloxyethyl (e.g. 1-methoxycarbonyloxyethyl, 1-ethoxycarbonyloxyethyl), a lower alkanoyloxymethyl group such as $C_2$–$C_7$ alkanoyloxymethyl (e.g. acetoxymethyl, propionyloxymethyl, butyryloxymethyl, pivaloyloxymethyl), an optionally substituted lower alkenyl group such as an optionally substituted $C_3$–$C_6$ allyl (e.g. allyl, 2-methylallyl, 3-methylally, cinnamyl), an optionally substituted arylmethyl group such as optionally substituted phenylmethyl (e.g. benzyl, p-methoxybenzyl, 2,4-dimethoxybenzyl, o-nitrobenzyl, p-nitrobenzyl, p-chlorobenzyl), an optionally substituted diarylmethyl group such as optionally substituted diphenylmethyl (e.g. diphenylmethyl, di-p-anisylmethyl), an optionally substituted aryl group such as an optionally substituted phenyl (e.g. phenyl, p-nitrophenyl, p-chlorophenyl, 2,6-dimethylphenyl), etc.

Specific examples of the protecting group for amino are a lower alkoxycarbonyl group such as a $C_1$–$C_5$ alkoxycarbonyl (e.g. t-butoxycarbonyl), a halogenated lower alkoxycarbonyl group such as $C_1$–$C_3$ alkoxycarbonyl substituted with one to three halogen atoms (e.g. 2-iodoethoxycarbonyl, 2,2,2-trichloroethoxycarbonyl), an optionally substituted arylmethoxycarbonyl group such as an optionally substituted phenylmethoxycarbonyl (e.g. benzyloxycarbonyl, o-nitrobenzyloxycarbonyl, p-nitrobenzyloxycarbonyl, p-methoxybenzyloxycarbonyl), an optionally substituted arylmethyl group such as an optionally substituted phenylmethyl group (e.g. benzyl, p-methoxybenzyl, 2,4-dimethoxybenzyl, o-nitrobenzyl, p-nitrobenzyl), an optionally substituted diarylmethyl group such as an optionally substituted diphenylmethyl (e.g. diphenylmethyl, di-p-anisylmethyl), an alpha-lower alkyl-benzyl group such as alpha-$C_1$–$C_4$ alkylbenzyl (e.g. alpha-methylbenzyl, alpha-ethylbenzyl), a trityl group, a substituted aryl group such as substituted phenyl (e.g. p-methoxyphenyl, 2,4-dimethoxyphenyl, o-nitrophenyl, p-nitrophenyl, 2,4-dinitrophenyl), a tri(lower)alkylsilyl group such as tri($C_1$–$C_4$)alkylsilyl (e.g. trimethylsilyl, t-butyldimethylsilyl, t-butyldiphenylmethylsilyl), a substituted methyl group (e.g. methoxymethyl, 2-methoxyethoxymethyl, benzyloxymethyl, methylthiomethyl), a tetrahydropyranyl group, etc.

When $R_2$ is a hydrogen atom, the beta-lactam compounds (I) are carboxylic acids, which may be converted into salts such as inorganic metal salts (e.g. lithium salt, sodium salt, potassium salt, calcium salt, magnesium salt), ammonium salt or organic ammonium salts (e.g. cyclohexylammonium salt, diisopropylammonium salt, triethylammonium salt). Among these salt, preferred are sodium salts, potassium salts, etc. Also, the beta-lactam compounds (I) may be converted into their acid addition salts. Examples of such acid addition salts are hydrochloride, sulfate, etc.

Of the beta-lactam compounds (I), those of the formula:

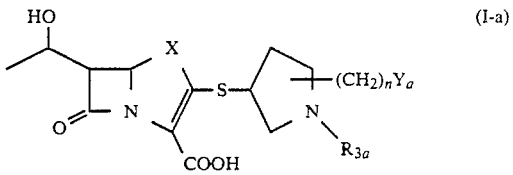

wherein X and n are each as defined above; $R_{3a}$ is the same as $R_3$ but does not represent a protective group for amino; and Ya is the same as Y but does not represent a protected amino group are preferred.

Depending upon the kind of the symbol X, the beta-lactam compounds (I) exhibit various characteristics with respect to physico-chemical stability, in vivo stability, anti-microbial activity, etc. When X represents a methylene group substituted with lower alkyl, the lower alkyl may be methyl, ethyl, n-propyl or the like, preferably methyl.

Some typical procedures for production of the beta-lactam compounds (I) are illustratively shown below.

Procedure I

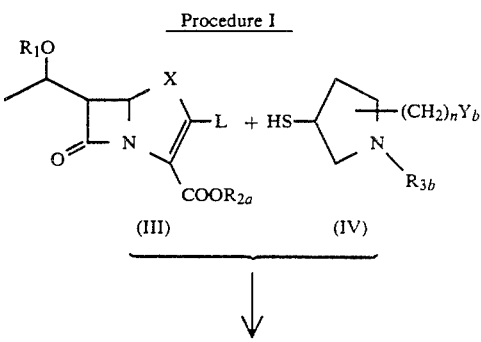

-continued
Procedure I

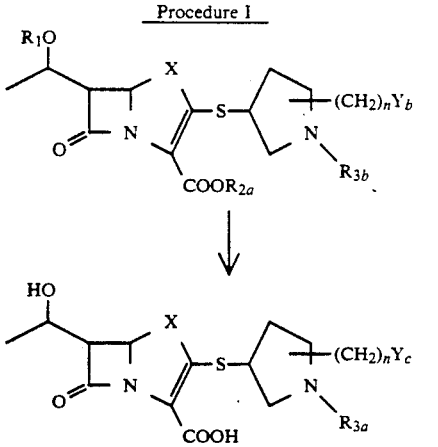

wherein $R_1$, X and n are each as defined above, $R_{2a}$ is a protective group for carboxyl, $R_{3b}$ is the same as $R_3$ but does not represent an amino group, $Y_b$ is the same as Y but does not represent the group (3), an amino group or a carboxyl group, $Y_c$ is the same as Y but does not represent the group (3) or a protected amino group and L is a leaving group such as a reactive ester of a hydroxyl group or a substituted or unsubstituted lower alkylsulfinyl group.

Thus, the beta-lactam compound (III) is reacted with the mercapto compound (IV) in a free or salt form in an inert solvent in the presence of a base, usually at a temperature of $-78°$ to $60°$ C., particularly of $-40°$ to $40°$ C., to give the beta-lactam compound (II).

As the leaving group represented by L in the beta-lactam compound (III), there may be exemplified various reactive esters of a hydroxyl group such as a substituted or unsubstituted arylsulfonic ester (e.g. benzenesulfonic ester, p-toluenesulfonic ester, p-nitrobenzenesulfonic ester, p-bromobenzenesulfonic ester), a lower alkanesulfonic ester (e.g. methanesulfonic ester, ethanesulfonic ester), a halo(lower)alkanesulfonic ester (e.g. trifluoromethanesulfonic ester), a diarylphosphoric ester (e.g. diphenylphosphoric ester) and an ester with a hydrogen halide, i.e. a halide (e.g. chloride, bromide, iodide). Among them, preferred are p-toluenesulfonic ester, methanesulfonic ester, diphenylphosphoric ester, etc. There may be also exemplified substituted or unsubstituted lower alkylsulfinyl groups, in which the lower alkyl moiety can be straight or branched alkyl preferably having 1 to 4 carbon atoms and examples of the substituent which may be present on such lower alkyl moiety are hydroxyl, lower alkoxy, lower alkoxycarbonyloxy, lower alkanoyloxy, amino, lower alkylamino, di(lower)alkylamino, lower alkanoylamino, lower alkoxycarbonylamino, ar(lower)alkyloxycarbonyloxy, ar(lower)alkyloxycarbonylamino, etc.

As the inert solvent, there may be exemplified dioxane, tetrahydrofuran, dimethylformamide, dimethylsulfoxide, acetonitrile, hexamethylphosphoramide, etc. Among them, acetonitrile or dimethylformamide is preferred. Examples of the base are sodium carbonate, potassium carbonate, sodium hydride, potassium hydride, potassium t-butoxide, pyridine, dimethylaminopyridine, triethylamine, diisopropylethylamine, etc. Particularly preferred is diisopropylethylamine.

The mercapto compound (IV) and the base are to be used in such amounts as can assure the proceeding of the reaction. Usually, the amount of the mercapto compound (IV) may be from 1 to 4.5 equivalents for the beta-lactam compound (III), and that of the base may be from 1 to 1.5 equivalents to the mercapto compound (IV).

After completion of the reaction, the beta-lactam compound (II) as the reaction product may be recovered from the reaction mixture by a per se conventional separation procedure.

When desired, the thus obtained beta-lactam compound (II) may be subjected to elimination of the protective group for hydroxy as $R_1$, elimination of the protective group for amino as $R_{3b}$ or $Y_b$ and/or elimination of the protective group for carboxyl as $Y_b$ or $R_{2a}$ to give the beta-lactam compound (I-b).

Elimination of the protective group for hydroxyl, carboxyl or amino may be accomplished by a per se conventional procedure which is appropriately chosen on the kind of the protective group. When, for instance, the protective group for hydroxy or amino is halo(lower)alkoxy-carbonyl or ar(lower)alkyloxycarbonyl or the protective group for carboxyl is halo(lower)alkyl, ar(lower)alkyl or benzhydryl, reduction may be applied for the elimination.

The reduction for elimination of halo(lower)alkoxycarbonyl or halo(lower)alkyl can be accomplished by treatment with a metal (e.g. zinc) in an organic solvent (e.g. acetic acid, tetrahydrofuran, methanol). The reduction for elimination of ar(lower)alkyloxycarbonyl, ar(lower)alkyl or benzhydryl can be achieved by catalytic reduction using a catalyst (e.g. platinum, palladium-carbon) in an inert solvent such as a lower alkanol (e.g. methanol, ethanol), an ether (e.g. tetrahydrofuran, dioxane) or an acid (e.g. acetic acid), or its mixture with any other solvent such as water or a buffer (e.g. phosphoric acid, morpholinopropanesulfonic acid). The catalytic reduction is normally performed at a temperature of $0°$ to $100°$ C., especially of $0°$ to $40°$ C., in a hydrogen atmosphere under an ordinary or elevated pressure.

When the protective group is o-nitrobenzyloxycarbonyl or o-nitrobenzyl, it can be eliminated by photo reaction.

When the protective group is lower alkenyloxycarbonyl (e.g. allyloxycarbonyl) or lower alkenyl (e.g. allyl), it can be eliminated by treatment with an organic solvent-soluble palladium complex catalyst having a coordinated phosphine ligand (e.g. tetraquis(triphenylphosphine) palladium) in the presence of a nucleophilic reagent (e.g. potassium 2-ethylhexanoate, sodium 2-ethylhexanoate, dimedone, pyrrolidine, piperidine) in an inert solvent such as a halogenated hydrocarbon (e.g. dichloromethane, chloroform), an aromatic hydrocarbon (e.g. benzene, toluene), an ether (e.g. diethyl ether, tetrahydrofuran, dioxane), an ester (e.g. ethyl acetate) or acetonitrile. The catalyst and the nucleophilic reagent may be used respectively in amounts of 0.01 to 0.5 equivalent and 1.0 to 8.0 equivalents to the beta-lactam compound (II). If necessary, triphenylphosphine may be added to the reaction system. The reaction temperature is preferred to be within a range of $-10°$ to $50°$ C.

After the reaction is completed, the produced beta-lactam compound (I-b) may be recovered from the reaction mixture by a per se conventional separation procedure. For instance, the reaction mixture is subjected to column chromatography using an adsorptive resin and elution of the desired product, followed by lyophilization.

lowed by elution and lyophilization of the desired product.

Procedure II

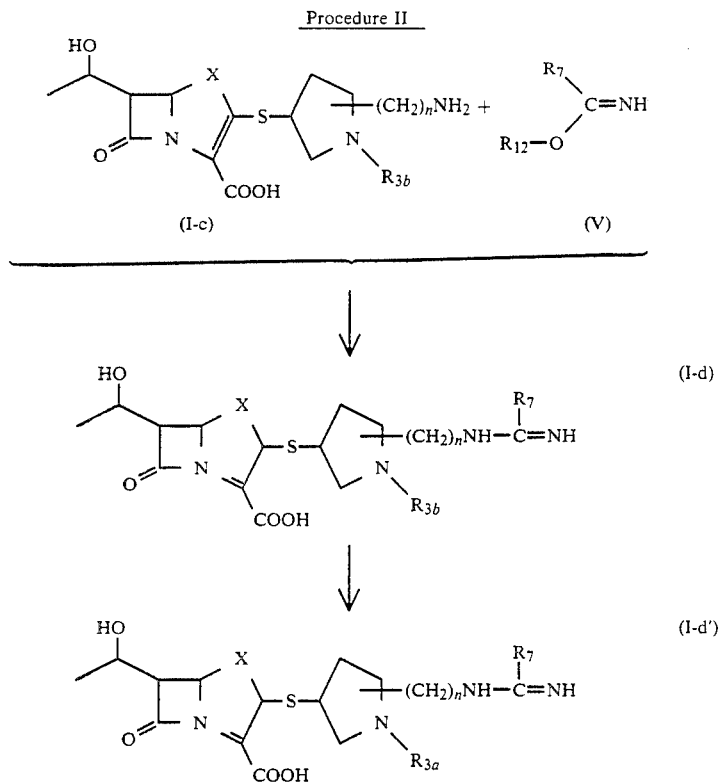

wherein X, $R_{3b}$, $R_7$ and n are each as defined above and $R_{12}$ is a lower alkyl group or a benzyl group.

Thus, the beta-lactam compound (I-c) is reacted with the imine (V) to give the beta-lactam compound (I-d), in the case of R3b being a protective group for amino, optionally followed by elimination of such protective group to give the beta-lactam compound (I-d').

The imine (V) may be used in a free form or an acid-addition salt form. When used in an acid-addition salt form, the acid portion may be constituted with a hydrohalogenic acid such as hydrochloric acid, hydrobromic acid or hydroiodic acid, and hydrochloric acid is particularly preferred. The reaction is normally carried out under a basic condition, i.e. at a pH of 8 to 14, preferably of 9 to 10. In order to keep the pH within this range, there may be used an alkaline agent such as an alkali metal hydroxide (e.g. sodium hydroxide, potassium hydroxide), an alkaline earth metal hydroxide (e.g. calcium hydroxide, barium hydroxide) or an alkali metal carbonate (e.g. sodium carbonate, potassium carbonate). Preferred are sodium hydroxide, potassium hydroxide, etc. Favorably, the reaction is effected using water as a solvent, but it may be also effected in a mixture of water with any organic solvent such as an alcohol (e.g. methanol, ethanol, n-propanol), an ether (e.g. tetrahydrofuran, dioxane), dimethylformamide or acetonitrile. The reaction may be controlled by heating or cooling, and an appropriate temperature therefor is usually from 0° C. to room temperature.

After completion of the reaction, the reaction mixture may be post-treated by a per se conventional procedure to recover the desired product. For instance, the reaction mixture is made neutral and then subjected to column chromatography using an adsorptive resin, fol- The beta-lactam compounds (I) of the invention have optical isomers as well as stereo isomers with respect to the asymmetric carbon atoms at the 5-, 6- and 8-positions and, in the case of X being a methylene group substituted with lower alkyl, also at the 4-position. For the sake of convenience, all these isomers are represented by a single plane formula; in other words, a single plane formula in this specification should be understood to cover all of the isomers or their mixtures. As to the steric configurations at the 5- and 6-positions, however, the compounds wherein the carbon atom at the 5-position has an R-configuration, i.e. those having a (5R,6S) or (5R,6R) configuration, are preferred when X is a methylene group or a sulfur atom, and those wherein the carbon atom at the 5-position has an S-configuration, i.e. those having a (5S,6S) or (5S,6R) configuration, are preferable when X is a methylene group substituted with lower alkyl. As to the steric configuration at the 8-position, those having an R-configuration are preferred. As to the steric configuration at the 4-position in case of X being a methylene group substituted with lower alkyl, there are present those having an R- or S-configuration, and preferred are those having an R-configuration.

Especially preferred are those having a (5R,6S,8R) configuration when X is a methylene group or a sulfur atom and those having a (4R,5S,6S,8R) configuration when X is a methylene group substituted with lower alkyl. In case of the former, the compounds are representable by either one of the following formulas:

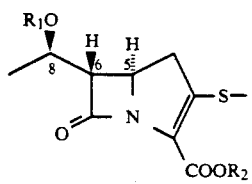

and

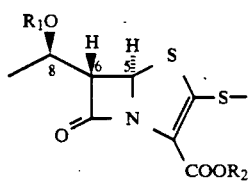

wherein $R_1$ and $R_2$ are each as defined above, and in case of the latter, the compounds are representable by the following formula:

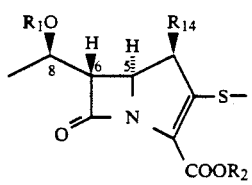

wherein $R_1$ and $R_2$ are each as defined above and $R_{14}$ is a lower alkyl group.

In reference to the substituent of the formula:

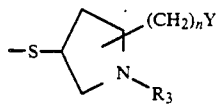

at the 3-position, the group of the formula: $-(CH_2)_nY$ may be present at any one of the 2'-, 4'- and 5'-positions, preferably at the 5'-position. In this case, the 5'-substituted pyrrolidin-3'-ylthio group has four isomers respectively having the (3'S,5'S) configuration, the (3'S,5'R) configuration, the (3'R,5'S) configuration and the (3'R,5'R) configuration, and all these are represented by a single plane formula. Among those configurations, particularly preferred are those having either one of the following formulas:

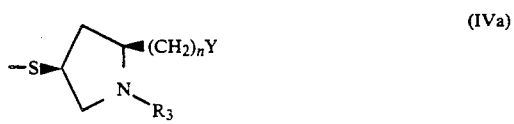 (IVa)

and

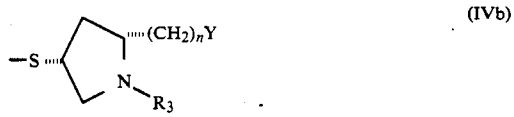 (IVb)

wherein Y, $R_3$ and n are each as defined above.

For production of the isomer having any steric configuration as stated above, any corresponding isomer of the mercapto compound (III) or (IV) may be employed as the starting compound.

Specific examples of the beta-lactam compounds (I) wherein $R_1$ and $R_2$ are each a hydrogen atom are shown in Tables 1 and 2 wherein Me is a methyl group, Et is an ethyl group, Pr is a propyl group and Ac is an acetyl group.

TABLE 1

| Compound No. | R  | Y        | $R_3$ | n |
|--------------|----|----------|-------|---|
| 1            | H  | $CONH_2$ | Me    | 0 |
| 2            | Me | $CONH_2$ | Me    | 0 |
| 3            | H  | CONHMe   | Me    | 0 |
| 4            | Me | CONHMe   | Me    | 0 |
| 5            | H  | $CONMe_2$| Me    | 0 |
| 6            | Me | $CONMe_2$| Me    | 0 |
| 7            | H  | CON⟨azetidinyl⟩ | Me | 0 |
| 8            | Me | CON⟨azetidinyl⟩ | Me | 0 |
| 9            | H  | CON⟨pyrrolidinyl⟩ | Me | 0 |

TABLE 1-continued
| Compound No. | R | Y | R₃ | n |
|---|---|---|---|---|
| 10 | Me | CON⟨4-ring⟩ | Me | 0 |
| 11 | H | CON⟨5-ring⟩ | Me | 0 |
| 12 | Me | CON⟨5-ring⟩ | Me | 0 |
| 13 | H | CON⟨6-ring⟩ | Me | 0 |
| 14 | Me | CON⟨6-ring⟩ | Me | 0 |
| 15 | H | COOMe | Me | 0 |
| 16 | Me | COOMe | Me | 0 |
| 17 | H | COOEt | Me | 0 |
| 18 | Me | COOEt | Me | 0 |
| 19 | H | COOH | Me | 0 |
| 20 | Me | COOH | Me | 0 |
| 21 | H | CN | Me | 0 |
| 22 | Me | CN | Me | 0 |
| 23 | H | CONHEt | Me | 0 |
| 24 | Me | CONHEt | Me | 0 |
| 25 | H | CONEt₂ | Me | 0 |
| 26 | Me | CONEt₂ | Me | 0 |
| 27 | H | CONH₂ | Me | 1 |
| 28 | Me | CONH₂ | Me | 1 |
| 29 | H | CONHMe | Me | 1 |
| 30 | Me | CONHMe | Me | 1 |
| 31 | H | CONMe₂ | Me | 1 |
| 32 | Me | CONMe₂ | Me | 1 |
| 33 | H | CON⟨3-ring⟩ | Me | 1 |
| 34 | Me | CON⟨3-ring⟩ | Me | 1 |
| 35 | H | CON⟨4-ring⟩ | Me | 1 |
| 36 | Me | CON⟨4-ring⟩ | Me | 1 |

TABLE 1-continued

Structure: carbapenem core with HO-CH(CH₃)- group, R substituent, S-linked pyrrolidine bearing (CH₂)ₙY and N-R₃, and COOH.

| Compound No. | R | Y | R₃ | n |
|---|---|---|---|---|
| 37 | H | CON(pyrrolidinyl) | Me | 1 |
| 38 | Me | CON(pyrrolidinyl) | Me | 1 |
| 39 | H | CON(piperidinyl) | Me | 1 |
| 40 | Me | CON(piperidinyl) | Me | 1 |
| 41 | H | CONHEt | Me | 1 |
| 42 | Me | CONHEt | Me | 1 |
| 43 | H | CONEt₂ | Me | 1 |
| 44 | Me | CONEt₂ | Me | 1 |
| 45 | H | COOMe | Me | 1 |
| 46 | Me | COOMe | Me | 1 |
| 47 | H | COOEt | Me | 1 |
| 48 | Me | COOEt | Me | 1 |
| 49 | H | COOH | Me | 1 |
| 50 | Me | COOH | Me | 1 |
| 51 | H | CN | Me | 1 |
| 52 | Me | CN | Me | 1 |
| 53 | H | NHCONH₂ | Me | 1 |
| 54 | Me | NHCONH₂ | Me | 1 |
| 55 | H | NHCONHMe | Me | 1 |
| 56 | Me | NHCONHMe | Me | 1 |
| 57 | H | NHCONMe₂ | Me | 1 |
| 58 | Me | NHCONMe₂ | Me | 1 |
| 59 | H | NHAc | Me | 1 |
| 60 | Me | NHAc | Me | 1 |
| 61 | H | NHCOOMe | Me | 1 |
| 62 | Me | NHCOOMe | Me | 1 |
| 63 | H | NHCOOEt | Me | 1 |
| 64 | Me | NHCOOEt | Me | 1 |
| 65 | H | OAc | Me | 1 |
| 66 | Me | OAc | Me | 1 |
| 67 | H | OCONH₂ | Me | 1 |
| 68 | Me | OCONH₂ | Me | 1 |
| 69 | H | OCONHMe | Me | 1 |
| 70 | Me | OCONHMe | Me | 1 |
| 71 | H | OCONMe₂ | Me | 1 |
| 72 | Me | OCONMe₂ | Me | 1 |
| 73 | H | NHCONHEt | Me | 1 |
| 74 | Me | NHCONHEt | Me | 1 |
| 75 | H | NHCONEt₂ | Me | 1 |
| 76 | Me | NHCONEt₂ | Me | 1 |
| 77 | H | OCONHEt | Me | 1 |
| 78 | Me | OCONHEt | Me | 1 |
| 79 | H | OCONEt₂ | Me | 1 |
| 80 | Me | OCONEt₂ | Me | 1 |
| 81 | H | OCOEt | Me | 1 |
| 82 | Me | OCOEt | Me | 1 |
| 83 | H | OCOOMe | Me | 1 |
| 84 | Me | OCOOMe | Me | 1 |
| 85 | H | OCOOEt | Me | 1 |
| 86 | Me | OCOOEt | Me | 1 |

TABLE 1-continued

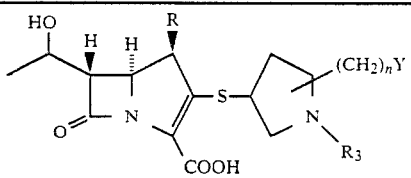

| Compound No. | R | Y | R₃ | n |
|---|---|---|---|---|
| 87 | H | CONH₂ | Me | 2 |
| 88 | Me | CONH₂ | Me | 2 |
| 89 | H | CONHMe | Me | 2 |
| 90 | Me | CONHMe | Me | 2 |
| 91 | H | CONMe₂ | Me | 2 |
| 92 | Me | CONMe₂ | Me | 2 |
| 93 | Me | CON⟨aziridine⟩ | Me | 2 |
| 94 | H | CON⟨aziridine⟩ | Me | 2 |
| 95 | H | CON⟨azetidine⟩ | Me | 2 |
| 96 | Me | CON⟨azetidine⟩ | Me | 2 |
| 97 | H | CON⟨pyrrolidine⟩ | Me | 2 |
| 98 | Me | CON⟨pyrrolidine⟩ | Me | 2 |
| 99 | H | CON⟨piperidine⟩ | Me | 2 |
| 100 | Me | CON⟨piperidine⟩ | Me | 2 |
| 101 | H | COOMe | Me | 2 |
| 102 | Me | COOMe | Me | 2 |
| 103 | H | COOEt | Me | 2 |
| 104 | Me | COOEt | Me | 2 |
| 105 | H | COOH | Me | 2 |
| 106 | Me | COOH | Me | 2 |
| 107 | H | CN | Me | 2 |
| 108 | Me | CN | Me | 2 |
| 109 | H | CONH₂ | Me | 3 |
| 110 | Me | CONH₂ | Me | 3 |
| 111 | H | CONHMe | Me | 3 |
| 112 | Me | CONHMe | Me | 3 |
| 113 | H | CONMe₂ | Me | 3 |
| 114 | Me | CONMe₂ | Me | 3 |
| 115 | H | CON⟨aziridine⟩ | Me | 3 |

TABLE 1-continued
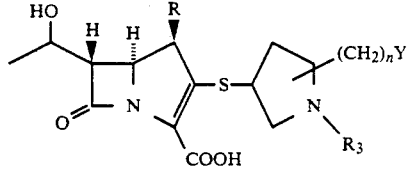
| Compound No. | R | Y | R₃ | n |
|---|---|---|---|---|
| 116 | Me | CON⟨△⟩ | Me | 3 |
| 117 | H | CON⟨□⟩ | Me | 3 |
| 118 | Me | CON⟨□⟩ | Me | 3 |
| 119 | H | CON⟨pentagon⟩ | Me | 3 |
| 120 | Me | CON⟨pentagon⟩ | Me | 3 |
| 121 | H | CON⟨hexagon⟩ | Me | 3 |
| 122 | Me | CON⟨hexagon⟩ | Me | 3 |
| 123 | H | COOMe | Me | 3 |
| 124 | Me | COOMe | Me | 3 |
| 125 | H | COOEt | Me | 3 |
| 126 | Me | COOEt | Me | 3 |
| 127 | H | COOH | Me | 3 |
| 128 | Me | COOH | Me | 3 |
| 129 | H | CN | Me | 3 |
| 130 | Me | CN | Me | 3 |
| 131 | H | CONH₂ | Me | 4 |
| 132 | Me | CONH₂ | Me | 4 |
| 133 | H | CONHMe | Me | 4 |
| 134 | Me | CONHMe | Me | 4 |
| 135 | H | CONMe₂ | Me | 4 |
| 136 | Me | CONMe₂ | Me | 4 |
| 137 | H | CON⟨△⟩ | Me | 4 |
| 138 | Me | CON⟨△⟩ | Me | 4 |
| 139 | H | CON⟨□⟩ | Me | 4 |

TABLE 1-continued

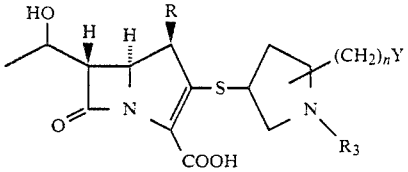

| Compound No. | R | Y | R₃ | n |
|---|---|---|---|---|
| 140 | Me | CON⟨azetidine⟩ | Me | 4 |
| 141 | H | CON⟨pyrrolidine⟩ | Me | 4 |
| 142 | Me | CON⟨pyrrolidine⟩ | Me | 4 |
| 143 | H | CON⟨piperidine⟩ | Me | 4 |
| 144 | Me | CON⟨piperidine⟩ | Me | 4 |
| 145 | Me | COOMe | Me | 4 |
| 146 | H | COOMe | Me | 4 |
| 147 | Me | COOEt | Me | 4 |
| 148 | H | COOEt | Me | 4 |
| 149 | H | COOH | Me | 4 |
| 150 | Me | COOH | Me | 4 |
| 151 | H | CN | Me | 4 |
| 152 | Me | CN | Me | 4 |
| 153 | H | CH=N—OMe | Me | 1 |
| 154 | Me | CH=N—OMe | Me | 1 |
| 155 | H | CH=N—OEt | Me | 1 |
| 156 | Me | CH=N—OEt | Me | 1 |
| 157 | H | CH=NNMe₂ | Me | 1 |
| 158 | Me | CH=NNMe₂ | Me | 1 |
| 159 | H | CH=NNEt₂ | Me | 1 |
| 160 | Me | CH=NNEt₂ | Me | 1 |
| 161 | H | CH=NN(Me)(Et) | Me | 1 |
| 162 | Me | CH=NN(Me)(Et) | Me | 1 |
| 163 | H | CH=NNHMe | Me | 1 |
| 164 | Me | CH=NNHMe | Me | 1 |
| 165 | H | CONHNH₂ | Me | 1 |
| 166 | Me | CONHNH₂ | Me | 1 |
| 167 | H | CONHNMe₂ | Me | 1 |
| 168 | Me | CONHNMe₂ | Me | 1 |
| 169 | H | CONMeNMe₂ | Me | 1 |
| 170 | Me | CONMeNMe₂ | Me | 1 |
| 171 | H | CONHNEt₂ | Me | 1 |
| 172 | Me | CONHNEt₂ | Me | 1 |

TABLE 1-continued

[Structure shown: bicyclic β-lactam core with HO-CH(Me)- group, H,H stereochemistry, R substituent, S linked to pyrrolidine bearing N-R₃ and (CH₂)ₙY, COOH]

| Compound No. | R | Y | R₃ | n |
|---|---|---|---|---|
| 173 | H | CONMeN(Me)(Et) | Me | 1 |
| 174 | Me | CONMeN(Me)(Et) | Me | 1 |
| 175 | H | OH | Me | 1 |
| 176 | Me | OH | Me | 1 |
| 177 | H | OMe | Me | 1 |
| 178 | Me | OMe | Me | 1 |
| 179 | H | OEt | Me | 1 |
| 180 | Me | OEt | Me | 1 |
| 181 | H | O-(n)Pr | Me | 1 |
| 182 | Me | O-(n)Pr | Me | 1 |
| 183 | H | O-(i)Pr | Me | 1 |
| 184 | Me | O-(i)Pr | Me | 1 |
| 185 | H | SMe | Me | 1 |
| 186 | Me | SMe | Me | 1 |
| 187 | H | SEt | Me | 1 |
| 188 | Me | SEt | Me | 1 |
| 189 | H | S-(n)Pr | Me | 1 |
| 190 | Me | S-(n)Pr | Me | 1 |
| 191 | H | S-(i)Pr | Me | 1 |
| 192 | Me | S-(i)Pr | Me | 1 |
| 193 | H | SO₂Me | Me | 1 |
| 194 | Me | SO₂Me | Me | 1 |
| 195 | H | SO₂Et | Me | 1 |
| 196 | Me | SO₂Et | Me | 1 |
| 197 | H | SO₂-(n)Pr | Me | 1 |
| 198 | Me | SO₂-(n)Pr | Me | 1 |
| 199 | H | SO₂-(i)Pr | Me | 1 |
| 200 | Me | SO₂-(i)Pr | Me | 1 |
| 201 | H | OH | Me | 2 |
| 202 | Me | OH | Me | 2 |
| 203 | H | OMe | Me | 2 |
| 204 | Me | OMe | Me | 2 |
| 205 | H | OH | Me | 3 |
| 206 | Me | OH | Me | 3 |
| 207 | H | OMe | Me | 3 |
| 208 | Me | OMe | Me | 3 |
| 209 | H | OH | Me | 4 |
| 210 | Me | OH | Me | 4 |
| 211 | H | OMe | Me | 4 |
| 212 | Me | OMe | Me | 4 |
| 213 | H | CONHMe | Et | 0 |
| 214 | Me | CONHMe | Et | 0 |
| 215 | H | CONMe₂ | Et | 0 |
| 216 | Me | CONMe₂ | Et | 0 |
| 217 | H | CONHMe | Et | 1 |
| 218 | Me | CONHMe | Et | 1 |
| 219 | H | CONHMe | Et | 2 |
| 220 | Me | CONHMe | Et | 2 |
| 221 | H | CONHMe | Et | 3 |
| 222 | Me | CONHMe | Et | 3 |
| 223 | H | CONHMe | Et | 4 |
| 224 | Me | CONHMe | Et | 4 |
| 225 | H | OH | Et | 1 |
| 226 | Me | OH | Et | 1 |
| 227 | H | OMe | Et | 1 |
| 228 | Me | OMe | Et | 1 |

TABLE 2

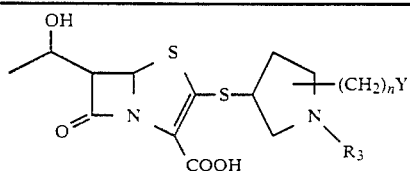

| Compound No. | R₃ | Y | n |
|---|---|---|---|
| 229 | Me | CONH₂ | 0 |
| 230 | Me | CONHMe | 0 |
| 231 | Me | CONMe₂ | 0 |
| 232 | Me | CON⊲ (aziridine) | 0 |
| 233 | Me | CON-azetidine | 0 |
| 234 | Me | CON-pyrrolidine | 0 |
| 235 | Me | CON-piperidine | 0 |
| 236 | Me | CONHEt | 0 |
| 237 | Me | CONEt₂ | 0 |
| 238 | Me | COOMe | 0 |
| 239 | Me | COOEt | 0 |
| 240 | Me | COOH | 0 |
| 241 | Me | CN | 0 |
| 242 | H | CONH₂ | 1 |
| 243 | Me | CONH₂ | 1 |
| 244 | H | CONHMe | 1 |
| 245 | Me | CONHMe | 1 |
| 246 | H | CONMe₂ | 1 |
| 247 | Me | CONMe₂ | 1 |
| 248 | H | CON⊲ (aziridine) | 1 |
| 249 | Me | CON⊲ (aziridine) | 1 |
| 250 | H | CON-azetidine | 1 |
| 251 | Me | CON-azetidine | 1 |
| 252 | H | CON-pyrrolidine | 1 |
| 253 | Me | CON-pyrrolidine | 1 |

TABLE 2-continued

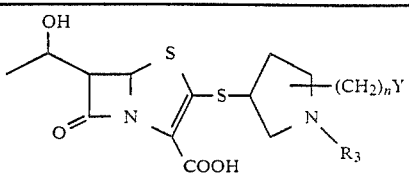

| Compound No. | R₃ | Y | n |
|---|---|---|---|
| 254 | H | CON-piperidine | 1 |
| 255 | Me | CON-piperidine | 1 |
| 256 | Me | CONHEt | 1 |
| 257 | H | CONHEt | 1 |
| 258 | H | CONEt₂ | 1 |
| 259 | Me | CONEt₂ | 1 |
| 260 | H | COOMe | 1 |
| 261 | Me | COOMe | 1 |
| 262 | H | COOEt | 1 |
| 263 | Me | COOEt | 1 |
| 264 | H | COOH | 1 |
| 265 | Me | COOH | 1 |
| 266 | H | CN | 1 |
| 267 | Me | CN | 1 |
| 268 | H | NHCONH₂ | 1 |
| 269 | Me | NHCONH₂ | 1 |
| 270 | H | NHCONHMe | 1 |
| 271 | Me | NHCONHMe | 1 |
| 272 | H | NHCONMe₂ | 1 |
| 273 | Me | NHCONMe₂ | 1 |
| 274 | H | NHAc | 1 |
| 275 | Me | NHAc | 1 |
| 276 | H | NHCOOMe | 1 |
| 277 | Me | NHCOOMe | 1 |
| 278 | H | NHCOOEt | 1 |
| 279 | Me | NHCOOEt | 1 |
| 280 | H | OAc | 1 |
| 281 | Me | OAc | 1 |
| 282 | H | OCONH₂ | 1 |
| 283 | Me | OCONH₂ | 1 |
| 284 | H | OCONHMe | 1 |
| 285 | Me | OCONHMe | 1 |
| 286 | H | OCONMe₂ | 1 |
| 287 | Me | OCONMe₂ | 1 |
| 288 | H | NHCONHEt | 1 |
| 289 | Me | NHCONHEt | 1 |
| 290 | H | NHCONEt₂ | 1 |
| 291 | Me | NHCONEt₂ | 1 |
| 292 | H | OCONHEt | 1 |
| 293 | Me | OCONHEt | 1 |
| 294 | H | OCONEt₂ | 1 |
| 295 | Me | OCONEt₂ | 1 |
| 296 | H | OCOEt | 1 |
| 297 | Me | OCOEt | 1 |
| 298 | H | OCOOMe | 1 |
| 299 | Me | OCOOMe | 1 |
| 300 | H | OCOOEt | 1 |
| 301 | Me | OCOOEt | 1 |
| 302 | H | CONH₂ | 2 |
| 303 | Me | CONH₂ | 2 |
| 304 | H | CONHMe | 2 |
| 305 | Me | CONHMe | 2 |
| 306 | H | CONMe₂ | 2 |
| 307 | Me | CON⊲ (aziridine) | 2 |

TABLE 2-continued

Structure: β-lactam core with OH-ethyl, S-pyrrolidine with N-R₃ and (CH₂)ₙY substituent, COOH group.

| Compound No. | R₃ | Y | n |
|---|---|---|---|
| 308 | H | CON(cyclopropyl) | 2 |
| 309 | Me | CON(azetidine) | 2 |
| 310 | H | CON(pyrrolidine) | 2 |
| 311 | Me | CON(pyrrolidine) | 2 |
| 312 | H | CON(piperidine) | 2 |
| 313 | Me | CON(piperidine) | 2 |
| 314 | H | COOMe | 2 |
| 315 | Me | COOMe | 2 |
| 316 | H | COOEt | 2 |
| 317 | Me | COOEt | 2 |
| 318 | H | COOH | 2 |
| 319 | Me | COOH | 2 |
| 320 | H | CN | 2 |
| 321 | Me | CN | 2 |
| 322 | H | CONH₂ | 3 |
| 323 | Me | CONH₂ | 3 |
| 324 | H | CONHMe | 3 |
| 325 | Me | CONHMe | 3 |
| 326 | H | CONMe₂ | 3 |
| 327 | Me | CONMe₂ | 3 |
| 328 | H | CON(cyclopropyl) | 3 |
| 329 | Me | CON(cyclopropyl) | 3 |
| 330 | H | CON(azetidine) | 3 |
| 331 | Me | CON(azetidine) | 3 |
| 332 | H | CON(pyrrolidine) | 3 |
| 333 | Me | CON(pyrrolidine) | 3 |
| 334 | H | CON(piperidine) | 3 |
| 335 | Me | CON(piperidine) | 3 |
| 336 | H | COOMe | 3 |
| 337 | Me | COOMe | 3 |
| 338 | H | COOEt | 3 |
| 339 | Me | COOEt | 3 |
| 340 | H | COOH | 3 |
| 341 | Me | COOH | 3 |
| 342 | H | CN | 3 |
| 343 | Me | CN | 3 |
| 344 | H | CONH₂ | 4 |
| 345 | Me | CONH₂ | 4 |
| 346 | H | CONHMe | 4 |
| 347 | Me | CONHMe | 4 |
| 348 | H | CONMe₂ | 4 |
| 349 | Me | CONMe₂ | 4 |
| 350 | H | CON(cyclopropyl) | 4 |
| 351 | Me | CON(cyclopropyl) | 4 |
| 352 | H | CON(azetidine) | 4 |
| 353 | Me | CON(azetidine) | 4 |
| 354 | H | CON(pyrrolidine) | 4 |
| 355 | Me | CON(pyrrolidine) | 4 |

TABLE 2-continued

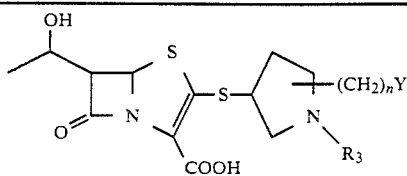

| Compound No. | R₃ | Y | n |
|---|---|---|---|
| 356 | H | (piperidine-CON) | 4 |
| 357 | Me | COOMe | 4 |
| 358 | H | COOMe | 4 |
| 359 | Me | COOEt | 4 |
| 360 | H | COOH | 4 |
| 361 | Me | COOH | 4 |
| 362 | H | CN | 4 |
| 363 | Me | CN | 4 |
| 364 | H | CH=N—OMe | 1 |
| 365 | Me | CH=N—OMe | 1 |
| 366 | H | CH=N—OEt | 1 |
| 367 | Me | CH=N—OEt | 1 |
| 368 | H | CH=NNMe₂ | 1 |
| 369 | Me | CH=NNMe₂ | 1 |
| 370 | H | CH=NNEt₂ | 1 |
| 371 | Me | CH=NNEt₂ | 1 |
| 372 | H | CH=NN(Me)(Et) | 1 |
| 373 | Me | CH=NN(Me)(Et) | 1 |
| 374 | H | CH=NNHMe | 1 |
| 375 | Me | CH=NNHMe | 1 |
| 376 | H | CONHNH₂ | 1 |
| 377 | Me | CONHNH₂ | 1 |
| 378 | H | CONHNMe₂ | 1 |
| 379 | Me | CONHNMe₂ | 1 |
| 380 | H | CONMeNMe₂ | 1 |
| 381 | Me | CONMeNMe₂ | 1 |
| 382 | H | CONHNEt₂ | 1 |
| 383 | Me | CONHNEt₂ | 1 |
| 384 | H | CONMeN(Me)(Et) | 1 |
| 385 | Me | CONMeN(Me)(Et) | 1 |
| 386 | H | OH | 1 |
| 387 | Me | OH | 1 |
| 388 | H | OMe | 1 |
| 389 | Me | OMe | 1 |
| 390 | H | OEt | 1 |
| 391 | Me | OEt | 1 |
| 392 | H | O-(n)Pr | 1 |
| 393 | Me | O-(n)Pr | 1 |
| 394 | H | O-(i)Pr | 1 |
| 395 | Me | O-(i)Pr | 1 |
| 396 | H | SMe | 1 |
| 397 | Me | SMe | 1 |
| 398 | H | SEt | 1 |
| 399 | Me | SEt | 1 |
| 400 | H | S-(n)Pr | 1 |
| 401 | Me | S-(n)Pr | 1 |

TABLE 2-continued

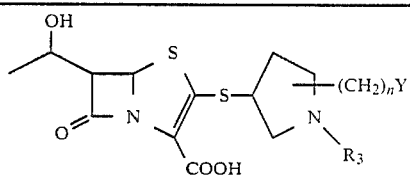

| Compound No. | R₃ | Y | n |
|---|---|---|---|
| 402 | H | S-(i)Pr | 1 |
| 403 | Me | S-(i)Pr | 1 |
| 404 | H | SO₂Me | 1 |
| 405 | Me | SO₂Me | 1 |
| 406 | H | SO₂Et | 1 |
| 407 | Me | SO₂Et | 1 |
| 408 | H | SO₂-(n)Pr | 1 |
| 409 | Me | SO₂-(n)Pr | 1 |
| 410 | H | SO₂-(i)Pr | 1 |
| 411 | Me | SO₂-(i)Pr | 1 |
| 412 | H | OH | 2 |
| 413 | Me | OH | 2 |
| 414 | H | OMe | 2 |
| 415 | Me | OMe | 2 |
| 416 | H | OH | 3 |
| 417 | Me | OH | 3 |
| 418 | H | OMe | 3 |
| 419 | Me | OMe | 3 |
| 420 | H | OH | 4 |
| 421 | Me | OH | 4 |
| 422 | H | OMe | 4 |
| 423 | Me | OMe | 4 |

As hereinbefore stated, the carbapenem compounds shown in Table 1 have stereo-isomers, among which are preferred are those having a carbapenem skeleton of the (4R, 5S, 6S, 8R) or (4R, 5S, 6R, 8R) configuration when R is a lower alkyl group and those having a carbapenem skeleton of the (5R, 6S, 8R) or (5R, 6R, 8R) configuration when R is a hydrogen atom. The penem compounds shown in Table 2 also have stereo-isomers, among which are favorable are those having a penem skeleton of the (5R, 6S, 8R) or (5R, 6R, 8R) configuration. With respect to the substituted pyrrolidinylthio group at the 3-position, those having a configuration represented by the formula (IVa) or (IVb) are preferred. All of these stereo-isomers fall within the scope of the invention.

The compound (III) as the starting material can be produced by reacting a compound of the formula:

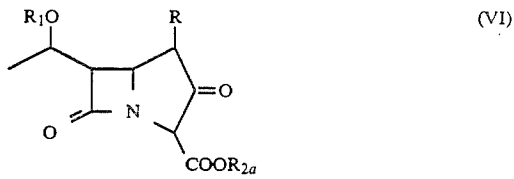

(VI)

wherein R₁ and R₂a are each as defined above and R is a hydrogen atom or a lower alkyl group with an optionally substituted arylsulfonylating agent (e.g. benzenesulfonyl chloride, p-toluenesulfonyl chloride, p-toluenesulfonic anhydride, p-nitrobenzenesulfonic anhydride, p-bromobenzenesulfonyl chloride), a lower alkanesulfonylating agent (e.g. methanesulfonic anhydride, methanesulfonyl chloride, ethanesulfonyl chloride), a halo(lower)alkanesulfonylating agent (e.g. trifluoromethanesulfonic anhydride, trifluoromethanesulfonyl chloride), a diarylphosphonylating agent (e.g. diphenyl chlorophosphate) or a halogenating agent (e.g. triphenylphosphine dichloride, triphenylphosphine dibromide, oxalyl chloride) in an inert solvent (e.g. methylene chloride, acetonitrile, dimethylformamide, tetrahydrofuran) in the presence of a base (e.g. triethylamine, diisopropylethylamine, N-dimethylaminopyridine).

Alternatively, the compound (III) may be produced by reacting a compound of the formula:

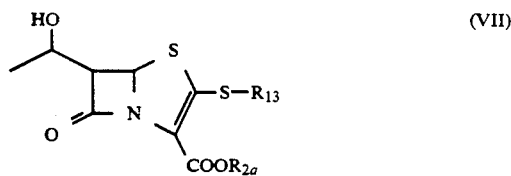

(VII)

wherein $R_{2a}$ is as defined above and $R_{13}$ is an optionally substituted lower alkyl group with an oxidizing agent. As the oxidizing agent, there is preferably used a relatively mild one such as perbenzoic acid, m-chloroperbenzoic acid, hydrogen peroxide, selenium dioxide or sodium m-periodate, particularly a substituted perbenzoic acid (e.g. chloroperbenzoic acid). Still, $R_{13}$ in the formula (VII) may correspond to the optionally substituted lower alkyl group in the optionally substituted lower alkylsulfinyl group represented by the symbol L in the formula (III).

The compound (VI) may be prepared by any conventional procedure as described in the following literatures when R is a hydrogen atom: (1) Japanese Patent Publication (unexamined) No. 27169/1980; (2) J.Am.-Chem.Soc., Vol. 103, 6765-6767 (1981); (3) J.Chem.-Soc., Perkin I, 964-968 (1981), etc., or in the following literatures when R is a lower alkyl group: (4) Heterocycles, Vol. 21, 29-40 (1984); (5) Japanese Patent Publication (unexamined) No. 26887/1983; (6) Japanese Patent Publication (unexamined) No. 104088/1985, etc. The compound (VII) may be also prepared by any conventional procedure as described in Japanese Patent Publications (unexamined) Nos. 9034/1980, 105686/1980, 81591/1981, etc.

The mercaptan compound (IV) as the other starting material can be produced by various processes, for instance, from trans-4-hydroxy-L-proline or cis-4-hydroxy-D-proline according to the procedure as described in European patent 182213.

The novel beta-lactam compounds (I) of the invention show remarkable antimicrobial activity against gram-positive and gram-negative bacteria such as *Staphylococcus aureus*, *Staphylococcus epidermides*, *Streptococcus pyrogens*, *Streptococcus faecalis*, *Escherichia coli*, *Proteus millabilis*, *Seratia malcescens* and *Pseudomonas aeruginosa* and are useful as anti-microbial agents, particularly effective in controlling gram-negative bacteria. They are also useful as intermediates in the synthesis of other anti-microbial agents. Especially, it may be noted that they exhibit a noticeable antimicrobial potency against beta-lactamase-producing bacteria.

While it is known that carbapenem compounds such as thienamycin are unstable to dehydropeptidase-I (DHP-I) in living bodies, particularly localized in kidneys, the beta-lactam compounds (I) are stable to DHP-I. In particular, those wherein X is a methylene group bearing a beta-methyl group are highly stable to DHP-I. In addition to these characteristics, it may be noted that they are relatively stable from the physico-chemical viewpoint.

In order to use the beta-lactam compounds (I) as anti-microbial agents for the treatment of diseases caused by pathogenic bacteria, they are normally administered parenterally or non-parenterally in per se conventional preparation forms such as tablets, capsules, powders, syrups or injections. Their doses depend upon the symptoms, ages and body weights of patients, the administration modes, the administration times, etc., and they may be normally given to adults in a daily dose of about 100 to 3,000 mg in one or more times.

The present invention will now be illustrated in greater detail with reference to the following Examples and Reference Examples, but it should be understood that these examples are given only for illustrative purposes and are not limitive of the present invention.

In the subsequent Examples and Reference Examples, the following abbreviations are used:

PNZ: p-nitrobenzyloxycarbonyl group
PMZ: p-methoxybenzyloxycarbonyl group
PMB: p-methoxybenzyl group
PNB: p-nitrobenzyl group
Ph: phenyl group
Ac: acetyl group
Ms: methanesulfonyl group
Ts: p-toluenesulfonyl group
TBDMS: t-butyldimethylsilyl group
Me: methyl group
Et: ethyl group
t-Bu: t-butyl group
Z: benzyloxycarbonyl group

EXAMPLE 1

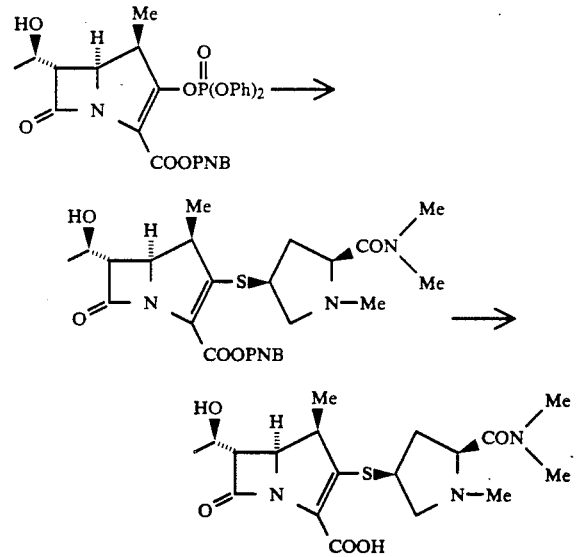

(a) (4R, 5R, 6S, 8R)-3-(Diphenylphosphoryloxy)-4-methyl-6-(1-hydroxyethyl)-1-azabicyclo[3.2.0]hept-2-en-7-one-2-carboxylic acid p-nitrobenzyl ester (139 mg) was dissolved in dry acetonitrile (1.2 ml), and diisopropylethylamine (51 mg) and a solution of 2S, 4S)-1-methyl-2-dimethylaminocarbonyl-4-mercaptopyrrolidine hydrochloride (88 mg) in dry acetonitrile (1 ml) were successively added thereto at −35° C. under nitrogen stream, followed by stirring at −5° to −10° C. for 2 hours. The reaction mixture was diluted with ethyl acetate, washed with sodium bicarbonate solution and water and dried over magnesium sulfate. The solvent was removed by distillation, and the residue was purified by silica gel thin layer chromatography to give (4R,5S,6S,8R,2′S,4′S)-3-[(1-methyl-2-dimethylaminocarbonylpyrrolidin)-4-ylthio]-4-methyl-6-(1-hydroxyethyl)-1-azabicyclo[3.2.0]hept-2-en-7-one-2-carboxylic acid p-nitrobenzyl ester (47 mg).

IR$_{max}^{neat}$ cm$^{-1}$: 1759, 1702, 1633, 1515, 1445.

NMR δ (CDCl$_3$): 1.27 (3H, d, J=7.3 Hz), 1.37 (3H, d, J=6.3 Hz), 2.34 (3H, s), 2.98 (3H, s), 3.16 (3H, s), 5.25 (1H, d, J=13.7 Hz), 5.48 (1H, d, J=13.7 Hz), 7.66 (2H, d, J=8.9 Hz).

(b) The above obtained (4R,5S,6S,8R,2′S,4′S)-3-[(1-methyl-2-dimethylaminocarbonylpyrrolidin)-4-ylthio]-4-methyl-6-(1-hydroxyethyl)-1-azabicyclo[3.2.0]hept-2-en-7-one-2-carboxylic acid p-nitrobenzyl ester (47 mg) was dissolved in tetrahydrofuran (2.6 ml), and 10% palladiumcarbon (38 mg) and morpholinopropanesulfonic acid buffer (pH, 7.0; 2.6 ml) were added thereto. The mixture was hydrogenated at room temperature for 5 hours under an atmospheric pressure of hydrogen. After removal of the catalyst, tetrahydrofuran was removed by distillation under reduced pressure. The remaining liquid was washed with dichloromethane, and the organic solvent was removed by distillation under reduced pressure. The resulting liquid was subjected to purification by polymer chromatography (CHP-20P), and the fractions eluted with 1% aqueous tetrahydrofuran solution were collected and lyophilized to give (4R,5S,6S,8R,2′S,4′S)-3-[(1-methyl-2-dimethylaminocarbonylpyrrolidine)-4-ylthio]-4-methyl-6-(1-hydroxyethyl)-1-azabicyclo[3.2.0]hept-2-en-7-one-2-carboxylic acid as white powder.

UV$_{max}^{H2O}$ nm: 301.

IR$_{max}^{KBr}$ cm$^{-1}$: 1755, 1640, 1600, 1388.

NMR δ (D$_2$O): 1.20 (3H, d, J=7.3 Hz), 1.29 (3H, d, J=6.3 Hz), 2.51 (3H, s), 2.97 (3H, s), 3.07 (3H, s).

EXAMPLE 2

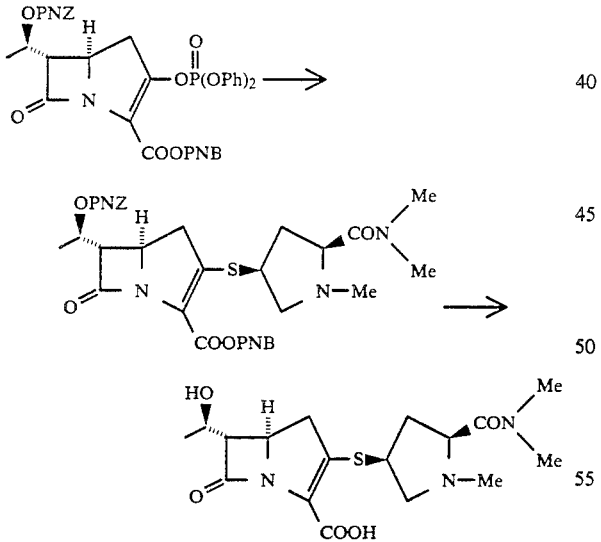

(a) (5R, 6S, 8R)-3-(Diphenylphosphoryloxy)-6-(1-p-nitrobenzyloxycarbonyloxyethyl)-1-azabicyclo[3.2.0]hept-2-en-7-one-2-carboxylic acid p-nitrobenzyl ester (205 mg) was dissolved in dry acetonitrile (1.7 ml), and diisopropylethylamine (166 mg) and a solution of (2S, 4S)-1-methyl-2-dimethylaminocarbonyl-4-mercaptopyrrolidine hydrochloride (145 mg) in dry acetonitrile (1.5 ml) were successively added thereto under nitrogen stream while ice-cooling, followed by stirring for 20 minutes. The reaction mixture was diluted with ethyl acetate, washed with sodium bicarbonate solution and water in order and dried over magnesium sulfate. The solvent was removed by distillation, and the residue was purified by silica gel thin layer chromatography to give (5R,6S,8R,2′S,4′S)-3-[(1-methyl-2-dimethylaminocarbonylpyrrolidin)-4-ylthio]-6-(1-p-nitrobenzyloxycarbonyloxyethyl)-1-azabicyclo[3.2.0]hept-2-en-7-one-2-carboxylic acid p-nitrobenzyl ester (160 mg).

IR$_{max}^{neat}$ cm$^{-1}$: 1779, 1750, 1703, 1648, 1523.

NMR δ (CDCl$_3$): 1.48 (3H, d, J=6.4 Hz), 2.35 (3H, s), 2.97 (3H, s), 3.15 (3H, s), 5.26 (2H, s), 5.44 (1H, d, J=13.9 Hz).

(b) The above obtained (5R,6S,8R,2′S,4′S)-3-[(1-methyl-2-dimethylaminocarbonylpyrrolidin)-4-ylthio]-6-(1-p-nitrobenzyloxycarbonyloxyethyl)-1-azabicyclo[3.2.0]hept-2-en-7-one-2-carboxylic acid p-nitrobenzyl ester (160 mg) was dissolved in tetrahydrofuran (7.4 ml), and 10% palladiumcarbon (240 mg) and a buffer solution of morpholinopropanesulfonic acid (pH, 7.0; 7.4 ml) were added thereto. The mixture was hydrogenated at room temperature for 3 hours under an atmospheric pressure of hydrogen. After removal of the catalyst, tetrahydrofuran was removed by distillation under reduced pressure, and the remaining liquid was washed with dichloromethane. The organic solvent contained therein was removed by distillation under reduced pressure. The resulting liquid was subjected to purification by polymer chromatography (CHP-20P), and the fractions eluted with 1% aqueous tetrahydrofuran solution were collected and lyophilized to give (5R,6S,8R,2′S,4′S)-3-[(1-methyl-2-dimethylaminocarbonylpyrrolidin)-4-ylthio]-6-(1-hydroxyethyl)-1-azabicyclo[3.2.0]hept-2-en-7-one-2-carboxylic acid as white powder.

UV$_{max}^{H2O}$ nm: 301.

IR$_{max}^{KBr}$ cm$^{-1}$: 1759, 1650, 1595, 1398.

NMR δ (D$_2$O): 1.28 (3H, d, J=6.3 Hz), 2.57 (3H, s), 2.97 (3H, s), 3.07 (3H, s).

EXAMPLE 3

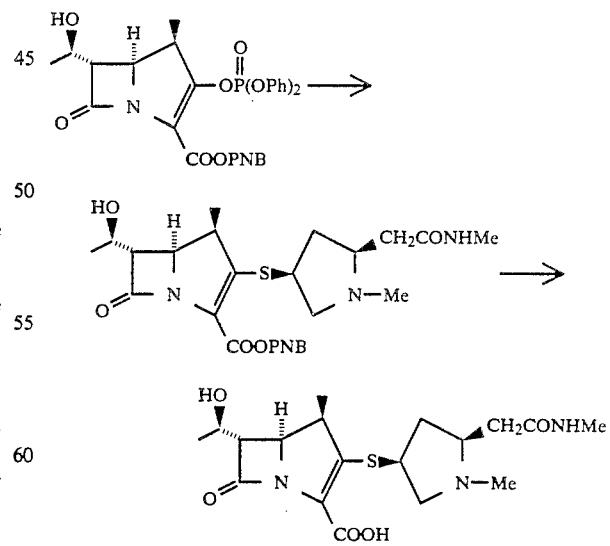

(a) (4R, 5R, 6S, 8R)-3-(Diphenylphosphoryloxy)-4-methyl-6-(1-hydroxyethyl)-1-azabicyclo[3.2.0]hept-2-en-7-one-2-carboxylic acid p-nitrobenzyl ester (142 mg) was dissolved in dry acetonitrile (1 ml), diisopropylethylamine (260 mg) and a solution of (2R,4R)-1-methyl-2-methylaminocarbonylmethyl-4-mercaptopyrrolidine hydrochloride (118 mg) in dry acetonitrile (1 ml) were added thereto at −45° C. under nitrogen stream, followed by stirring at −20° to −40° C. for 1 hour. The reaction mixture was diluted with ethyl acetate, washed with aqueous sodium bicarbonate solution and aqueous sodium chloride in order and dried over magnesium sulfate. The solvent was removed, and the residue was purified by silica gel thin layer chromatography to give (4R,5S,6S,8R,2′R,4′R)-3-[(1-methyl-2-methylaminocarbonylmethylpyrrolidin)-4ylthio]-4-methyl-6-(1-hydroxyethyl)-1-azabicyclo[3.2.0]hept-2-en-7-one-2-carboxylic acid p-nitrobenzyl ester (27 mg).

IR$_{max}^{neat}$ cm$^{-1}$: 1760, 1705, 1643, 1520, 1343.

NMR δ (CDCl$_3$) 1.27 (3H, d, J=7 Hz), 1.35 (3H, d, J=7.5 Hz), 2.32 (3H, s), 2.81 (3H, d, J=4.8 Hz), 5.24 (1H, d, J=14 Hz), 5.48 (1H, d, J=14 Hz), 7.66 (2H, d, J =8.8 Hz), 8.21 (2H, d, J=8.8 Hz).

(b) The above obtained (4R,5S,6S,8R,2′R,4′R)-3-[(-1-methyl-2-methylaminocarbonylmethylpyrrolidin)-4-yl-thio]-4-methyl-6-(1-hydroxyethyl)-1-azabicyclo[3.2.0]hept-2-en-7-one-2-carboxylic acid p-nitrobenzyl ester (27 mg) was dissolved in tetrahydrofuran (2.7 ml), and 10% palladiumcarbon (40 mg) and water (2.7 ml) were added thereto. The mixture was hydrogenated at room temperature for 5 hours under an atmospheric pressure of hydrogen. After removal of the catalyst, tetrahydrofuran was removed by distillation under reduced pressure, and the remaining liquid was washed with dichloromethane. The organic solvent contained therein was removed by distillation under reduced pressure. The resulting liquid was subjected to purification by polymer chromatography (CHP-20P), and the fractions eluted with 1% aqueous tetrahydrofuran solution were collected and lyophilized to give (4R,5S,6S,8R,2′R,4′R)-3-[(1-methyl-2-methylaminocarbonylmethylpyrrolidin) -4-ylthio]-6-(1-hydroxyethyl)-1-azabicyclo[3.2.0]hept-2-en-7-one-2-carboxylic acid as white powder.

UV$_{max}^{H2O}$ nm: 298.

IR $_{max}^{KBr}$ cm$^{-1}$: 1745, 1640, 1583, 1378.

NMR δ (D$_2$O): 1.21 (3H, d, J=7.3 Hz), 1.29 (3H, d, J=6.3 Hz), 2.76 (3H, s), 2.94 (3H, s), 3.48 (1H, dd, J =2.6 and 6 Hz).

EXAMPLE 4

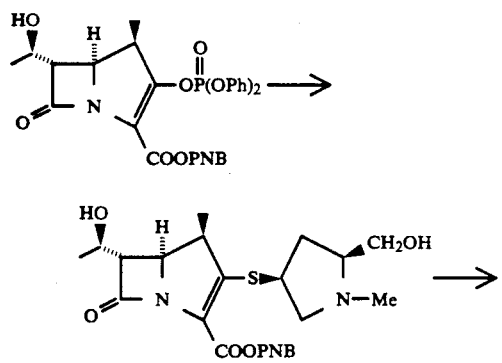

-continued

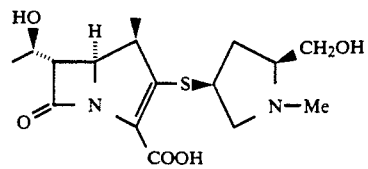

(a) (4R,5R,6S,8R)-3-(Diphenylphosphoryloxy)-4-methyl-6-(1-hydroxyethyl)-1-azabicyclo[3.2.0]hept-2-en-7-one-2-carboxylic acid p-nitrobenzyl ester (183 mg) was dissolved in dry acetonitrile (1.2 ml), and a solution of (2S,4S)-1-methyl-2-hydroxymethyl-4-mercaptopyrrolidine hydrochloride (183 mg) in dry acetonitrile (1 ml) and diisopropylethylamine (297 mg) were added thereto at −45° C. under nitrogen stream, followed by stirring at −20° to −40° C. for 1 hour. The reaction mixture was diluted with ethyl acetate, washed with aqueous sodium bicarbonate solution and aqueous sodium chloride solution in order and dried over magnesium sulfate. The solvent was removed by distillation, and the residue was purified by silica gel thin layer chromatography to give (4R,5S,6S,8R,2′S,4′S)-3-[(1-methyl-2-hydroxymethylpyrrolidin)-4-ylthio]-4-methyl-6-(1-hydroxyethyl)-1-azabicyclo[3.2.0]hept-2-en-7-one-2-carboxylic acid p-nitrobenzyl ester (87 mg).

IR$_{max}^{neat}$ cm$^{-1}$: 1760, 1705, 1522, 1305, 1212.

NMR δ (CDCl$_3$) 1.27 (3H, d, J=6.8 Hz), 1.34 (3H, d, J=5.9 Hz), 2.32 (3H, s), 5.22 (1H, d, J=14 Hz), 5.48 (1H, d, J=14 Hz), 7.66 (2H, d, J=8.6 Hz), 8.19 (2H, d, J=8.6 Hz).

(b) The above obtained (4R,5S,6S,8R,2′S,4′S)-3-[(1-methyl-2-hydroxymethylpyrrolidin)-4-ylthio]-4-methyl-6-(1-hydroxyethyl)-1-azabicyclo[3.2.0]hept-2-en-7-one-2-carboxylic acid p-nitrobenzyl ester (87 mg) was dissolved in tetrahydrofuran (4 ml), and 10% palladiumcarbon (131 mg) and a buffer solution of morphorinopropanesulfonic acid (pH, 7.0; 4 ml) were added thereto. The mixture was hydrogenated at room temperature for 5 hours under an atmospheric pressure of hydrogen. After removal of the catalyst, tetrahydrofuran was removed by distillation under reduced pressure, and the remaining liquid was washed with dichloromethane. The organic solvent contained therein was removed by distillation under reduced pressure. The remaining liquid was subjected to purification by polymer chromatography (CHP-20P), and the fractions eluted with 1% aqueous tetrahydrofuran solution were collected and lyophilized to give (4R,5S,6S,8R,2′S,4′S)-3-[(1-methyl-2-hydroxymethylpyrrolidin)-4-ylthio]-4-methyl-6-(1-hydroxyethyl)-1-azabicyclo[3.2.0]hept-2-en-7-one-2-carboxylic acid as white powder.

UV$_{max}^{H2O}$ nm: 298.

IR $_{max}^{KBr}$ cm$^{-1}$: 1750, 1595, 1445, 1388.

NMR δ (D$_2$O): 1.21 (3H, d, J=7.3 Hz), 1.29 (3H, d, J=6.3 Hz), 2.73 (3H, s), 3.82 (2H, d, J=5 Hz).

EXAMPLES 5 TO 10

In the same manner as in Example 1, 3 or 4, the compounds as shown in Table 3 were obtained.

TABLE 3

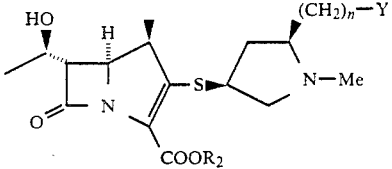

| Example No. | R₂ | Y | n | | Physical data |
|---|---|---|---|---|---|
| 5 | PNB | COOMe | 0 | IR$_{max}^{neat}$ cm$^{-1}$:<br>NMR δ (CDCl₃): | 1760, 1740, 1552, 1445, 1345, 1205.<br>1.31(3H, d, J=7.3Hz), 2.45(3H, s), 3.79(3H, s), 5.30(1H, d, J=14Hz), 5.50(1H, d, J=14Hz), 7.71(2H, d, 8.8Hz), 8.25(2H, d, J=8.8Hz). |
|  | H | COOMe | 0 | UV$_{max}^{H2O}$ nm:<br>IR$_{max}^{KBr}$ cm$^{-1}$:<br>NMR δ (D₂O): | 303.<br>1740, 1593, 1445, 1388, 1180.<br>1.20(3H, d, J=7.3Hz), 1.30(3H, d, J=6.3Hz), 2.37(3H, s), 3.42(1H, dd, J=2.3 & 6.3Hz), 3.78(3H, s). |
| 6 | PNB | CONHMe | 2 | IR$_{max}^{neat}$ cm$^{-1}$:<br>NMR δ (CDCl₃): | 1760, 1705, 1650, 1523, 1450, 1323.<br>1.35(3H, d, J=6.4Hz), 2.26(3H, s), 2.77(3H, d, J=4.6Hz), 5.23(1H, d, J=13.9Hz), 5.47(1H, d, J=13.9Hz), 7.66 (2H, d, J=8.8Hz), 8.19(2H, d, J=8.8Hz). |
|  | H | CONHMe | 2 | UV$_{max}^{H2O}$ nm:<br>IR$_{max}^{KBr}$ cm$^{-1}$:<br>NMR δ (D₂O): | 298.<br>1756, 1645, 1597, 1457, 1390.<br>1.21(3H, d, J=7.3Hz), 1.29(3H, d, J=6.3Hz), 2.73(3H, s), 2.74(3H, s). |
| 7 | PNB | CN | 1 | IR$_{max}^{neat}$ cm$^{-1}$:<br>NMR δ (CDCl₃): | 2250, 1760, 1700, 1522, 1344.<br>1.27(3H, d, J=7.3Hz), 1.35(3H, d, J=6.6Hz), 2.35(3H, s), 5.24(1H, d, J=13.9Hz), 5.47(1H, d, J=13.9Hz), 7.66(2H, d, J=8.8Hz), 8.20(2H, d, 8.8Hz). |
| 7 | H | CN | 1 | UV$_{max}^{H2O}$ nm:<br>IR$_{max}^{KBr}$ cm$^{-1}$:<br>NMR δ (D₂O): | 298.<br>2250, 1758, 1598, 1450, 1383.<br>1.22(3H, d, J=7.3Hz), 1.29(3H, d, J=6.6Hz), 3.01(3H, s). |
| 8 | PNB | CONHMe | 0 | IR$_{max}^{neat}$ cm$^{-1}$:<br>NMR δ (CDCl₃): | 1760, 1705, 1660, 1520, 1445, 1270, 1205, 1130, 1042.<br>1.27(3H, d, J=7.7Hz), 1.35(3H, d, J=6.8Hz), 2.36(3H, s), 2.83(3H, d, J=4.8Hz), 5.23(1H, d, J=13.9Hz), 5.49(1H, d, J=13.9Hz), 7.66(2H, d, J=8.6Hz), 8.20(2H, d, J=8.6Hz). |
|  | H | CONHMe | 0 | UV$_{max}^{H2O}$ nm:<br>IR$_{max}^{KBr}$ cm$^{-1}$:<br>NMR δ (D₂O): | 301.<br>1750, 1650, 1595, 1448, 1390.<br>1.17(3H, d, J=7.3Hz), 1.29(3H, d, J=6.3Hz), 2.32(3H, s), 2.79(3H, s), 3.42(1H, dd, J=2.5 & 6Hz), 4.19(1H, dd, J=2.5 & 9.0Hz). |
| 9 | PNB | CONH₂ | 0 | IR$_{max}^{neat}$ cm$^{-1}$:<br>NMR δ (CDCl₃): | 1765, 1680, 1520, 1450, 1340.<br>1.28(3H, d, J=7.0Hz), 1.35(3H, d, J=6.2Hz), 2.39(3H, s), 5.23(1H, d, J=14Hz), 5.49(1H, d, J=14Hz), 6.04 (1H, broad s), 7.13(1H, broad s), 8.20(2H, d, J=8.6Hz). |
|  | H | CONH₂ | 0 | UV$_{max}^{H2O}$ nm:<br>IR$_{max}^{KBr}$ cm$^{-1}$:<br>NMR δ (D₂O): | 301.<br>1750, 1675, 1595, 1450, 1390.<br>1.20(3H, d, J=7.3Hz), 1.29(3H, d, J=6.3Hz), 2.35(3H, s), 3.42(1H, dd, J=2.0 & 6.0Hz), 4.19(1H, dd, J=2.0 & 9.0Hz). |
| 10 | PNB |  | 0 | IR$_{max}^{neat}$ cm$^{-1}$:<br>NMR δ (CDCl₃): | 1760, 1702, 1630, 1520, 1445, 1340, 1205, 1130, 1040.<br>1.26(3H, d, J=7.0Hz), 1.34(3H, d, J=7.0Hz), 2.33(3H, s), 5.26(1H, d, J=14Hz), 5.45(1H, d, J=14Hz), 7.67 (2H, d, J=8.8Hz), 8.20(2H, d, J=8.8Hz). |
| 10 | H | 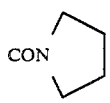 | 0 | UV$_{max}^{H2O}$ nm:<br>IR$_{max}^{KBr}$ cm$^{-1}$:<br>NMR δ (D₂O): | 301.<br>1755, 1610, 1453, 1388, 1255.<br>1.20(3H, d, J=7.3Hz), 1.29(3H, d, J=6.3Hz), 2.34(3H, s), 4.19(1H, dd, J=2.0 & 9.0Hz). |

EXAMPLE 11

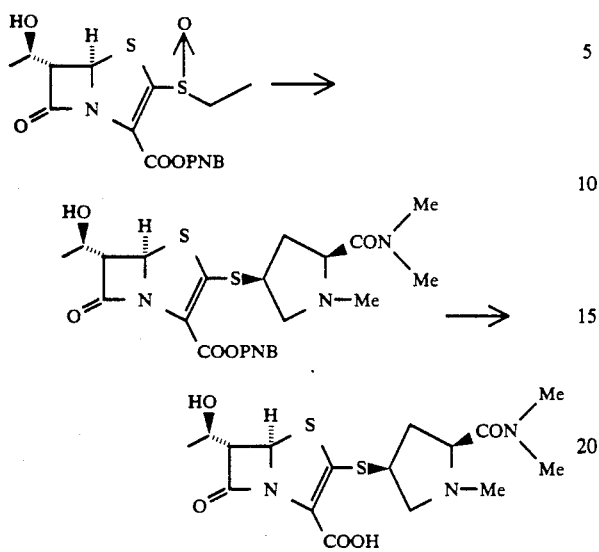

(a) (5R,6S,8R)-2-Ethylsulfinyl-6-(1-hydroxyethyl)-penem-3-carboxylic acid p-nitrobenzyl ester (70 mg) was dissolved in dry acetonitrile (1.5 ml), and diisopropylethylamine (64 mg) and a solution of (2'S,4'S)-1-methyl-2-dimethylaminocarbonyl-4-mercaptopyrrolidine hydrochloride (111 mg) in dry acetonitrile (1 ml) were successively added thereto at −40° C. under nitrogen stream, followed by stirring at −25° to −40° C. for 15 minutes. The reaction mixture was diluted with ethyl acetate, washed with aqueous sodium bicarbonate solution and aqueous sodium chloride solution in order and dried over magnesium sulfate. The solvent was removed by distillation, and the residue was crystallized from ethyl acetate to give (5R,6S,8R,2'S,4'S)-2-[(1-methyl-2-dimethylaminocarbonyl)pyrrolidin-4-ylthio]-6-(1-hydroxyethyl)penem-3-carboxylic acid p-nitrobenzyl ester (62 mg).

IR $_{max}^{Nujol}$ cm$^{-1}$: 1764, 1680, 1640, 1520, 1482.

NMR δ (CDCl$_3$) 1.38 (3H, d, J=6.3 Hz), 2.36 (3H, s), 2.97 (3H, s), 3.14 (3H, s), 3.74 (1H, dd, J=1.7 and 6.9 Hz), 5.23 (1H, d, J=14 Hz), 5.45 (1H, d, J=14 Hz), 5.68 (1H, d, J=1.7 Hz).

(b) The above obtained (5R,6S,8R,2'S,4'S)-2-[(1-methyl-2-dimethylaminocarbonyl) pyrrolidin-4-ylthio]-6-(1-hydroxyethyl)penem-3-carboxylic acid p-nitrobenzyl ester (54 mg) was dissolved in tetrahydrofuran (4 ml), and 10% palladium-carbon (41 mg) and a buffer solution of 0.1 M phosphoric acid (pH, 6.86; 4 ml) were added thereto. The mixture was hydrogenated at room temperature for 4.5 hours under an atmospheric pressure of hydrogen. After removal of the catalyst, tetrahydrofuran was removed by distillation under reduced pressure, and the remaining liquid was washed with dichloromethane. The organic solvent contained therein was removed by distillation under reduced pressure. The resulting liquid was subjected to purification by polymer chromatography (CHP-20P). The fractions eluted with 1% aqueous tetrahydrofuran solution were collected and lyophilized to give (5R,6S,8R,2'S,4'S)-2-(1-methyl-2-dimethylaminocarbonyl)pyrrolidin-4-ylthio)-6-(1-hydroxyethyl)penem-3-carboxylic acid.

UV $_{max}^{H2O}$ nm: 322, 256.

IR $_{max}^{KBr}$ cm$^{-1}$: 1769, 1639, 1592, 1508, 1363.

NMR δ (D2O): 1.30 (3H, d, J=6.3 Hz), 2.45 (3H, s), 2.96 (3H, s), 3.07 (3H, s), 3.91 (1H, dd, J=1.7 and 6 Hz), 5.69 (1H, d, J=1.7 Hz).

EXAMPLE 12

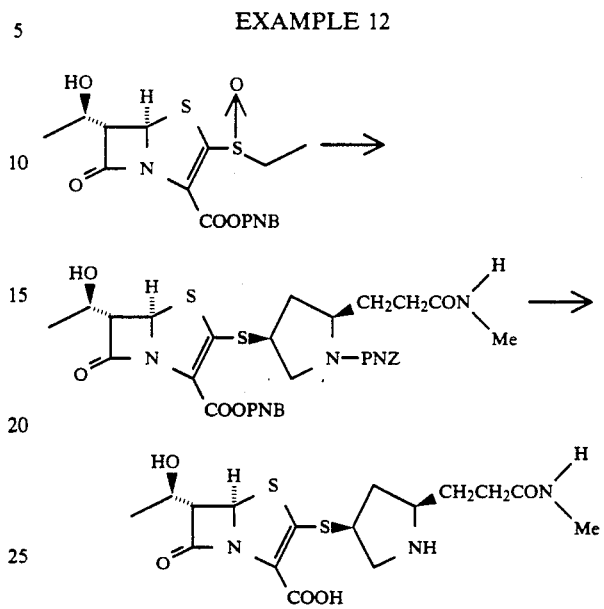

(a) (5R,6S,8R)-2-Ethylsulfinyl-6-(1-hydroxyethyl)-penem-3-carboxylic acid p-nitrobenzyl ester (80 mg) was dissolved in dry acetonitrile (3 ml), and diisopropylethylamine (54 mg) and (2R,4S)-1-p-nitrobenzyloxycarbonyl-2-(2-methylaminocarbonylethyl)-4-mercaptopyrrolidine (152 mg) were successively added thereto at −40° C. under nitrogen stream, followed by stirring at −30° to −40° C. for 30 minutes. The reaction mixture was diluted with ethyl acetate, washed with aqueous sodium phosphate solution and aqueous sodium chloride solution in order and dried over magnesium sulfate. The solvent was removed by distillation, and the residue was crystallized from ethyl acetate to give (5R,6S,8R,2'R,4'S)-2-{[(1-p-nitrobenzyloxycarbonyl)-2-(2-methylaminocarbonylethyl)pyrrolidin]-4-ylthio}-6-(1-hydroxyethyl)penem-3-carboxylic acid p-nitrobenzyl ester (72 mg).

IR $_{max}^{Nujol}$ cm$^{-1}$: 1780, 1702, 1642, 1523.

NMR δ (DMSO-d ): 1.17 (3H, d, J=6.3 Hz), 3.31 (3H, d, J=6.3 Hz), 5.22 (2H, s), 5.43 (1H, d, J=13.9 Hz), 5.80 (1H, d, J=1.3 Hz), 8.23 (4H, d, J=8.8 Hz).

(b) The above obtained (5R,6S,8R,2'R,4'S)-2-{[(1-p-nitrobenzyloxycarbonyl)-2-(2-methylaminocarbonylethyl)pyrrolidin]-4-ylthio}-6-(1-hydroxyethyl)penem-3-carboxylic acid p-nitrobenzyl ester (72 mg) was dissolved in a mixture of tetrahydrofuran (2.4 ml) and dimethylformamide (0.8 ml), and 10% palladium-carbon (108 mg) and a buffer solution of phosphoric acid (pH, 7.0; 3.2 ml) were added thereto. The mixture was hydrogenated at room temperature for 7 hours under an atmospheric pressure of hydrogen. After removal of the catalyst by filtration, tetrahydrofuran was removed by distillation under reduced pressure, and the remaining liquid was washed with dichloromethane. The organic solvent contained therein was removed by distillation under reduced pressure. The resulting liquid was subjected to purification by polymer chromatography(CHP-20P). The fractions eluted with 2% aqueous tetrahydrofuran solution were collected and lyophilized to give (5R,6S,8R,2'R,4'S)-2-{[2-(2-methylaminocarbonylethyl)pyrrolidin]-4-ylthio}-6-(1-hydroxyethyl)-penem-3-carboxylic acid.

UV $_{max}^{H2O}$ nm: 323,256.

IR $_{max}^{KBr}$ cm$^{-1}$: 1772, 1640, 1580, 1368.

NMR δ (D$_2$O): 1.31 (3H, d, J=6.6 Hz), 2.38 (2H, t, J=7.6 Hz), 2.73 (3H, s), 5.71 (1H, d, J=1.3 Hz).

EXAMPLES 13 TO 15

In the same manner as in Example 12, the compounds shown in Table 4 were obtained.

TABLE 4

| Example No. | R$_2$ | R$^o$ | R$_3$ | n | Physical data | |
|---|---|---|---|---|---|---|
| 13 | PNB | N(Me)(Me) | PNZ | 2 | IR$_{max}^{neat}$ cm$^{-1}$: | 1779, 1702, 1635, 1520. |
| | | | | | NMR δ (CDCl$_3$): | 1.37(3H, d, J=6.2Hz), 2.91(3H, s), 2.94(3H, s), 5.21(2H, s), 5.44 (1H, d, J=13.6Hz), 5.71(1H, d, J= 1.3Hz), 8.20(4H, d, J=8.6Hz). |
| | H | N(Me)(Me) | H | 2 | UV$_{max}^{H2O}$ nm: | 323, 256. |
| | | | | | IR$_{max}^{KBr}$ cm$^{-1}$: | 1768, 1623, 1585(sh), 1368. |
| | | | | | NMR δ (D$_2$O): | 1.31(3H, d, J=6.3Hz), 2.93(3H, s), 3.07(3H, s), 5.72(1H, d, J=1.3Hz). |
| 14 | PNB | N(Me)(Me) | PNZ | 1 | IR$_{max}^{neat}$ cm$^{-1}$: | 1793, 1703, 1641, 1525, 1401. |
| | | | | | NMR δ (CDCl$_3$): | 1.37(3H, d, J=6.2Hz), 2.91(18/5H, s), 2.95(12/5H, s), 5.22(2H, s), 5.43(1H, d, J=13.9Hz), 5.70(1H, d, J=1.1Hz). |
| | H | N(Me)(Me) | H | 1 | UV$_{max}^{H2O}$ nm: | 321, 256. |
| | | | | | IR$_{max}^{KBr}$ cm$^{-1}$: | 1772, 1630, 1595(sh), 1370. |
| | | | | | NMR δ (D$_2$O): | 1.31(3H, d, J=6.6Hz), 2.93(3H, s), 3.05(3H, s), 5.72(1H, d, J=1.3Hz). |
| 15 | PNB | NH(Me) | PNZ | 1 | IR$_{max}^{Nujol}$ cm$^{-1}$: | 1779, 1703, 1675, 1630, 1519. |
| | | | | | NMR δ (DMSO-d$_6$): | 3.32(3H, d, J=6.3Hz), 5.23(2H, s), 5.43(1H, d, J=14Hz), 5.79(1H, d, 1.3Hz), 8.23(4H, d, J=8.6Hz). |
| 15 | H | NH(Me) | H | 1 | UV$_{max}^{H2O}$ nm: | 323, 256. |
| | | | | | IR$_{max}^{KBr}$ cm$^{-1}$: | 1768, 1642, 1580, 1365. |
| | | | | | NMR δ (D$_2$O): | 1.30(3H, d, J=6.6Hz), 2.74(3H, s), 5.72(1H, d, J=1.3Hz). |

REFERENCE EXAMPLE 1-1

Sodium bicarbonate (131.04 g) was dissolved in water (1040 ml), and trans-4-hydroxy-L-proline (78.6 g) was added thereto. To the resultant mixture, a solution of benzyloxycarbonyl chloride (72 ml) in dry toluene (320 ml) was added, and the mixture was stirred at an inner temperature of 28° C. for 3 hours. Sodium bicarbonate (65.52 g) and benzyloxycarbonyl chloride (72 ml) were additionally added thereto, and stirring was continued at the same temperature for 2 hours. The reaction mixture was washed with ether, and the aqueous layer was filtered. The filtrate was washed again with ether. The aqueous layer was adjusted to pH 1 with 6N hydrochloric acid and extracted with ethyl acetate. The extract was washed with aqueous sodium chloride solution, dried over sodium sulfate and concentrated to remove the solvent to give trans-1-benzyloxycarbonyl-4-hydroxy-L-proline.

IR$_{max}^{neat}$ cm$^{-1}$: 1710, 1690, 1430, 1352, 1205.

REFERENCE EXAMPLE 1-2

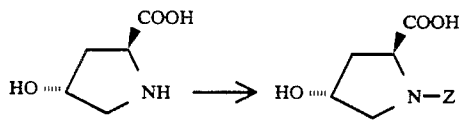

trans-1-Benzyloxycarbonyl-4-hydroxy-L-proline (26.5 g) was dissolved in dry dichloromethane (419 ml), and triethylamine (20.9 ml) was added thereto, followed by addition of sec-butyl chloroformate (20.45 g) at 0 to 10° C. under nitrogen stream. The resultant mixture was stirred at the same temperature for 1 hour. To the reaction mixture, a solution of dimethylamine (18.18 g) in dry dichloromethane (63 ml) was added at 0 to 10° C., and stirring was continued at the same temperature for 1 hour. The reaction mixture was successively washed with dilute hydrochloric acid, aqueous sodium chloride solution, aqueous sodium bicarbonate solution and aqueous sodium chloride solution in order and dried over magnesium sulfate. After removal of the solvent by distillation, the residue was purified by silica gel column chromatography to give (2S,4R)-1-benzyloxycarbonyl-2-dimethylaminocarbonyl-4-hydroxypyrrolidine.

IR$_{max}^{neat}$ cm$^{-1}$: 1699, 1637, 1415, 1352.

REFERENCE EXAMPLE 1-3

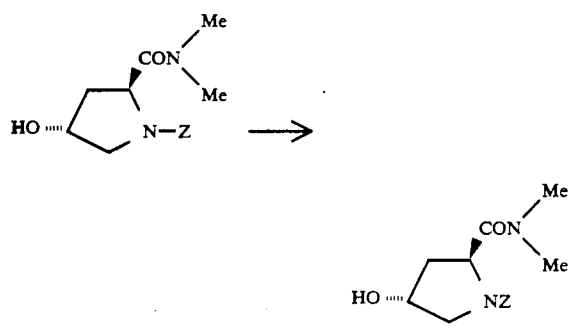

To a solution of (2S,4R)-1-benzyloxycarbonyl-2-dimethylaminocarbonyl-4-hydroxypyrrolidine (5.97 g) in ethanol (60 ml), 10% palladium-carbon (containing water 50 (1.20 g) was added, and the mixture was hydrogenated at room temperature for 3 hours under an atmospheric pressure of hydrogen. After removal of the catalyst by filtration, the filtrate was evaporated to remove the solvent to give (2S,4R)-2-dimethylaminocarbonyl-4-hydroxypyrrolidine.

IR$_{max}^{KBr}$ cm$^{-1}$: 1642, 1500, 1387, 1221, 1100.

REFERENCE EXAMPLE 1-4

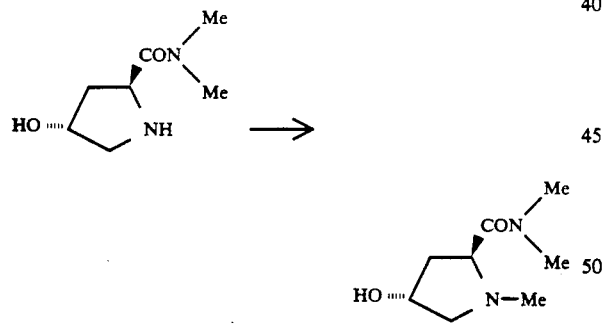

To a solution of (2S,4R)-2-dimethylaminocarbonyl-4-hydroxypyrrolidine (2.0 g) in acetic acid (14.4 ml) and water (8 ml), 37% aqueous formaldehyde solution (1.27 g) and platinum oxide (38 mg) were added, and the mixture was hydrogenated at room temperature for 7 hours under an atmospheric pressure of hydrogen. The reaction mixture was filtered, and the filtrate was evaporated under reduced pressure to remove the solvent. The residue was dissolved in dichloromethane and dried over magnesium sulfate. Potassium carbonate (3.5 g) was added thereto, and the mixture was stirred for 1.5 hours, followed by filtration. Removal of the solvent gave (2S,4R)-1-methyl-2-dimethylaminocarbonyl-4-hydroxypyrrolidine.

IR$_{max}^{neat}$ cm$^{-1}$: 1630, 1498, 1445, 1399, 1338.

REFERENCE EXAMPLE 1-5

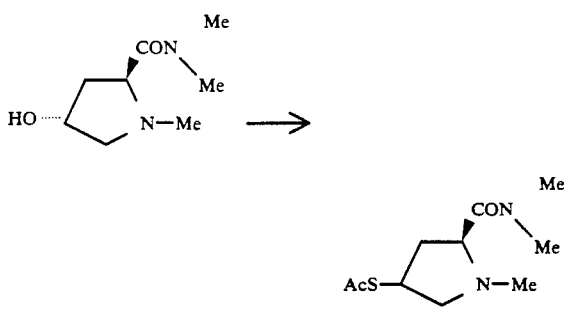

(2S,4R)-1-Methyl-2-dimethylaminocarbonyl-4-hydroxypyrrolidine (970 mg) was dissolved in dry tetrahydrofuran (11.1 ml), and triphenylphosphine (2.66 g) was added thereto. To the resultant mixture, diethyl azodicarboxylate (1.60 ml) was added under nitrogen steam while ice-cooling, and the mixture was stirred for 30 minutes. Thioacetic acid (1.45 ml) was added to the mixture under ice-cooling, and stirring was continued for 40 minutes under ice-cooling, followed by allowing to stand overnight. The reaction mixture was diluted with dichloromethane, washed with aqueous potassium carbonate solution and dried over magnesium sulfate. After removal of the solvent by distillation, the residue was purified by silica gel column chromatography to give (2S,4S)-1-methyl-2-dimethylaminocarbonyl-4-acetylthiopyrrolidine.

IR $_{max}^{neat}$ cm$^{-1}$: 1685, 1640, 1495, 1450, 1395.

REFERENCE EXAMPLE 1-6

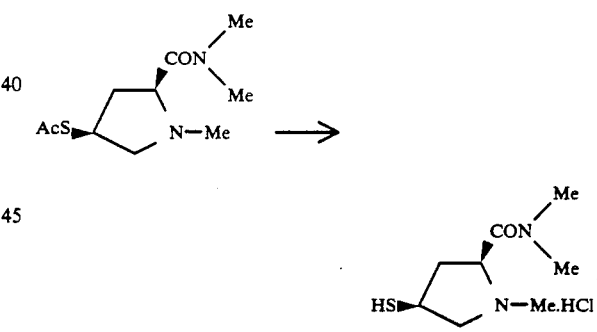

(2S,4S)-1-Methyl-2-dimethylaminocarbonyl-4-acetylthiopyrrolidine (660 mg) was dissolved in methanol (6.6 ml), and a solution of sodium methoxide (155 mg) in methanol (2.2 ml) was added thereto at room temperature under nitrogen stream, followed by stirring at the same temperature for 3 minutes. To the reaction mixture, 6N hydrochloric acid (1.05 ml) was added, and the solvent was removed by distillation. The residue was dissolved in ethanol (10.5 ml), and active carbon (99 mg) was added thereto under reflux. After refluxing for 15 minutes, the resultant mixture was filtered while hot, and the filtrate was concentrated under reduced pressure. The residue was dissolved in dichloromethane and dried over magnesium sulfate. Removal of the solvent gave (2S,4S)-1-methyl-2-dimethylaminocarbonyl-4-mercaptopyrrolidine hydrochloride.

IR$_{max}^{neat}$ cm$^{-1}$: 1658, 1505, 1450, 1363, 1260.

REFERENCE EXAMPLE 2-1

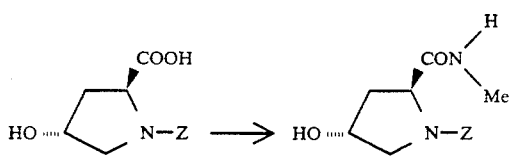

trans-1-Benzyloxycarbonyl-4-hydroxy-L-proline (3.06 g) was dissolved in dry dichloromethane (48 ml), and triethylamine (1.75 ml) was added thereto, followed by addition of ethyl chloroformate (1.88 g) at −50° C. under nitrogen stream. The resultant mixture was stirred at −30° to −50° C. for 30 minutes, and a solution of methylamine (1.44 g) in dichloromethane (5 ml) and methanol (3.7 ml) was added thereto at −50° C. Stirring was continued at −30° to −50° C. for 20 minutes. The reaction mixture was successively washed with dilute hydrochloric acid, aqueous sodium chloride solution, dilute sodium hydroxide solution and sodium chloride solution and dried over magnesium sulfate. After removal of the solvent, the residue was crystallized from ether to give (2S,4R)-1-benzyloxycarbonyl-2-methylaminocarbonyl-4-hydroxypyrrolidine.

IR$_{max}^{Nujol}$ cm$^{-1}$: 1680 (sh), 1658, 1572, 1439, 1358.

REFERENCE EXAMPLE 2-2

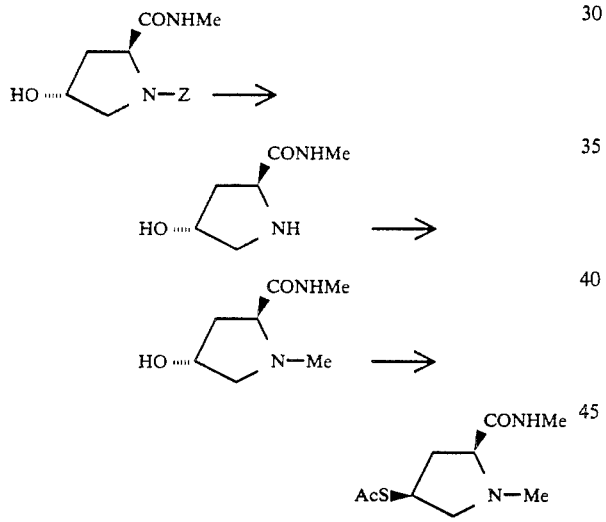

In the same manner as in Reference Examples 1-3, 1-4 and 1-5, there was produced (2S,4S)-1-methyl-2-methylaminocarbonyl-4-acetylthiopyrrolidine from (2S,4R)-1-benzyloxycarbonyl-2-methylaminocarbonyl-4-hydroxypyrrolidine (951 mg).

IR$_{max}^{neat}$ cm$^{-1}$: 1678, 1648, 1520, 1392.

REFERENCE EXAMPLE 2-3

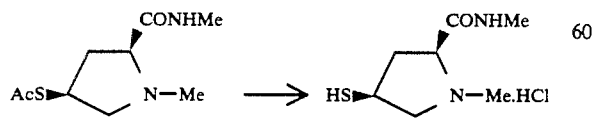

(2S,4S)-1-Methyl-2-methylaminocarbonyl-4-acetylthiopyrrolidine (215 mg) was dissolved in methanol (2.4 ml), and a solution of sodium methoxide (54 mg) in methanol (1.2 ml) was added thereto at room temperature under nitrogen stream, followed by stirring at the same temperature for 3 minutes. To the reaction mixture, 6N hydrochloric acid (0.38 ml) was added, and the solvent was distilled off. The residue was dissolved in a mixture of dichloromethane and methanol (4:1) and dried over magnesium sulfate. Removal of the solvent gave (2S,4S)-1-methyl-2-methylaminocarbonyl4-mercaptopyrrolidine hydrochloride.

IR$_{max}^{KBr}$ cm$^{-1}$: 1678, 1562, 1438, 1119.

REFERENCE EXAMPLE 3-1

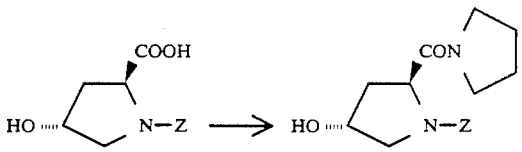

trans-1-Benzyloxycarbonyl-4-hydroxy-L-proline (2.48 g) was dissolved in dry dichloromethane (39 ml), and triethylamine (1.95 ml) was added thereto, followed by addition of sec-butyl chloroformate (1.92 g) at 0° to 5° C. under nitrogen stream. The resultant mixture was stirred at the same temperature for 15 minutes, and pyrrolidine (2.62 g) was further added thereto. The resulting mixture was stirred at the same temperature for 40 minutes and then at temperature for 1 hour. The reaction mixture was successively washed with dilute hydrochloric acid, aqueous sodium chloride solution, aqueous sodium hydroxide solution and aqueous sodium chloride solution in order and dried over magnesium sulfate. After removal of the solvent, the residue was purified by silica gel column chromatography to give (2S,4R)-1-benzyloxycarbonyl-2-(1-pyrrolidinecarbonyl)-4-hydroxypyrrolidine.

$_{max}^{neat}$ cm$^{-1}$: 1700, 1630, 1415, 1350, 1115.

REFERENCE EXAMPLE 3-2

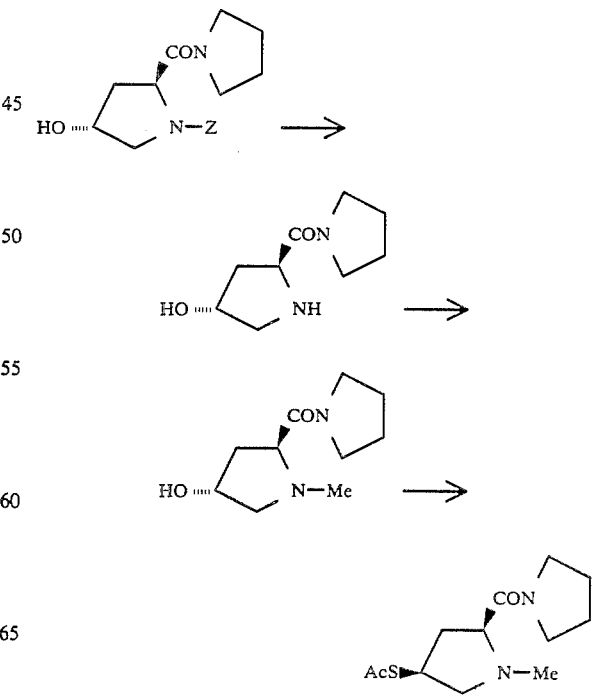

In the same manner as in Reference Examples 1-3, 1-4 and 1-5, there was produced (2S,4S)-1-methyl-2-(1-pyrrolidinecarbonyl)-4-acetylthiopyrrolidine from (2S,4R)-1-benzyloxycarbonyl-2-(1-pyrrolidinecarbonyl)-4-hydroxypyrrolidine (2.58 g).

IR$_{max}^{neat}$ cm$^{-1}$: 1682, 1637, 1436, 1340, 1110.

REFERENCE EXAMPLE 3-3

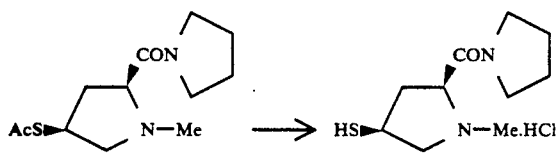

(2S,4S)-1-Methyl-2-(1-pyrrolidinecarbonyl)-4-acetylthiopyrrolidine (283 mg) was dissolved in methanol (2.8 ml), and a solution of sodium methoxide (62 mg) in methanol (1.2 ml) was added thereto at room temperature under nitrogen stream, followed by stirring at the same temperature for 3 minutes. To the reaction mixture, conc. hydrochloric acid (177 mg) was added, and the solvent was distilled off. The residue was dissolved in dichloromethane and dried over magnesium sulfate. Removal of the solvent gave (2S,4S)-1-methyl-2-(1-pyrrolidinecarbonyl)-4-mercaptopyrrolidine hydrochloride.

IR$_{max}^{neat}$ cm$^{-1}$: 1640, 1445, 1360, 1230.

REFERENCE EXAMPLE 4-1

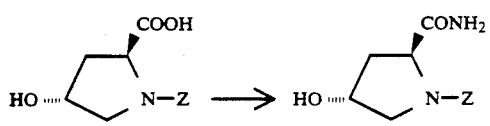

trans-1-Benzyloxycarbonyl-4-hydroxy-L-proline (3.55 g) was dissolved in dry tetrahydrofuran (60 ml), and triethylamine (2.80 ml) was added thereto, followed by addition of sec-butyl chloroformate (2.75 g) at 0° to 5° C. under nitrogen stream. The resultant mixture was stirred at the same temperature for 30 minutes and cooled to −50° C. 28 Aqueous ammonia (3.62 ml) was added thereto, and the resulting mixture was stirred at the same temperature for 30 minutes, followed by removal of the solvent. The residue was diluted with ethyl acetate and dried over magnesium sulfate. After removal of the solvent, the residue was purified by silica gel column chromatography to give (2S,4R)-1-benzyloxycarbonyl-2-aminocarbonyl-4-hydroxypyrrolidine.

IR$_{max}^{neat}$ cm$^{-1}$: 1685 (sh), 1670, 1415, 1350, 1116.

REFERENCE EXAMPLE 4-2

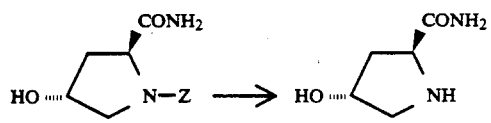

In the same manner as in Reference Example 1-3, there was produced (2S,4R)-2-aminocarbonyl-4-hydroxypyrrolidine from (2S,4R)-1-benzyloxycarbonyl-2-aminocarbonyl-4-hydroxypyrrolidine (3.0 g).

IR$_{max}^{KBr}$ cm$^{-1}$: 1693, 1407, 1359, 1303, 1188.

REFERENCE EXAMPLE 4-3

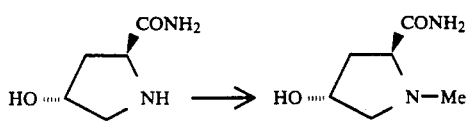

To a solution of (2S,4R)-2-aminocarbonyl4-hydroxypyrrolidine (1.40 g) in acetic acid (12.4 ml) and water (6.8 ml), 37% aqueous formaldehyde solution (1.09 g) and platinum oxide (33 mg) were added, and the mixture was vigorously stirred at room temperature for 16 hours under an atmospheric pressure of hydrogen. The reaction mixture was filtered, followed by removal of the solvent. The residue was dissolved in isopropanol, and magnesium sulfate and potassium carbonate were added thereto. The resultant mixture was stirred at room temperature for 1 hour and filtered. After removal of the solvent, the residue was purified by silica gel column chromatography to give (2S,4R)-1-methyl-2-aminocarbonyl-4-hydroxypyrrolidine.

IR$_{max}^{Nujol}$ cm$^{-1}$: 1635, 1455, 1375, 1304, 1184.

REFERENCE EXAMPLE 4-4

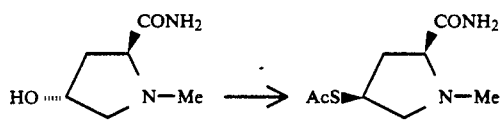

(2S,4R)-1-Methyl-2-aminocarbonyl-4-hydroxypyrrolidine (540 mg) was dissolved in dry dimethylformamide (10 ml), and triphenylphosphine (1.78 g) was added thereto. To the resultant mixture, diethyl azodicarboxylate (1.07 ml) was added under nitrogen steam while ice-cooling, and the mixture was stirred for 35 minutes. Thioacetic acid (0.76 ml) was added to the mixture under ice-cooling, and stirring was continued for 30 minutes under ice-cooling and at room temperature for 4 hours. The reaction mixture was diluted with dichloromethane, washed with aqueous sodium bicarbonate solution and dried over magnesium sulfate. After removal of the solvent, the residue was purified by silica gel column chromatography to give (2S,4S)-1-methyl-2-aminocarbonyl-4-acetylthiopyrrolidine.

IR$_{max}^{Nujol}$ cm$^{-1}$: 1680, 1647, 1442, 1370, 1135.

REFERENCE EXAMPLE 4-5

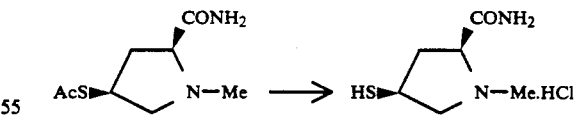

(2S,4S)-1-Methyl-2-aminocarbonyl-4-acetylthiopyrrolidine (201 mg) was dissolved in methanol (2.4 ml), and a solution of sodium methoxide (54 mg) in methanol (1.2 ml) was added thereto at room temperature under nitrogen stream, followed by stirring at the same temperature for 5 minutes. To the reaction mixture, conc. hydrochloric acid (240 mg) was added, and the solvent was removed. The residue was dissolved in a mixture of chloroform and methanol (4:1) and dried over magnesium sulfate. Removal of the solvent gave (2S,4S)-1-methyl-2-aminocarbonyl-4-mercaptopyrrolidine hydrochloride.

IR$_{max}^{Nujol}$ cm$^{-1}$: 1684, 1629, 1450, 1373, 1316.

REFERENCE EXAMPLE 5-1

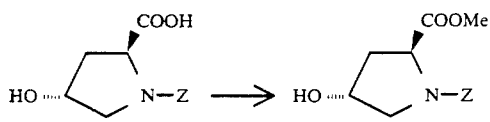

To a solution of trans-1-benzyloxycarbonyl-4-hydroxy-L-proline (138 g) in methanol (1380 ml), conc. sulfuric acid (9.92 g) was added, and the resultant mixture was refluxed for 2 hours. The reaction mixture was neutralized with 1N aqueous sodium hydroxide solution, and methanol was removed therefrom. The residue was diluted with ethyl acetate, washed with aqueous sodium chloride solution and dried over magnesium sulfate. Removal of the solvent gave trans-1-benzyloxycarbonyl-4-hydroxy-L-proline methyl ester.

IR$_{max}^{neat}$ cm$^{-1}$: 1745, 1700, 1425, 1355, 1210.

REFERENCE EXAMPLE 5-2

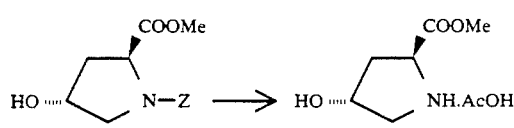

To a solution of (2S,4R)-1-benzyloxycarbonyl-2-methoxycarbonyl-4-hydroxypyrrolidine (4.34 g) in 95% ethanol (44 ml), 10% palladium-carbon (419 mg) and acetic acid (0.89 ml) were added. The mixture was vigorously stirred at room temperature for 1.5 hours under an atmospheric pressure of hydrogen. Removal of the catalyst gave (2S,4R)-2-methoxycarbonyl-4-hydroxypyrrolidine acetate.

IR$_{max}^{neat}$ cm$^{-1}$: 1745, 1585, 1420, 1240.

REFERENCE EXAMPLE 5-3

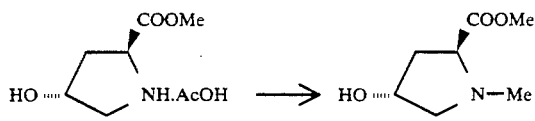

In the same manner as in Reference Example 1-4, there was produced (2S,4R)-1-methyl-2-methoxycarbonyl-4-hydroxypyrrolidine from (2S,4R)-2-methoxycarbonyl-4-hydroxypyrrolidine acetate (2.96 g).

IR$_{max}^{neat}$ cm$^{-1}$: 1738, 1439, 1340, 1272, 1200.

REFERENCE EXAMPLE 5-4

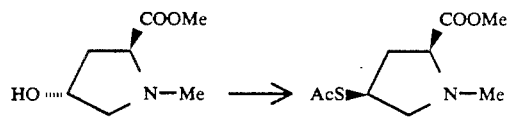

(2S,4R)-1-Methyl-2-methoxycarbonyl-4-hydroxypyrrolidine (795 mg) was dissolved in dry tetrahydrofuran (10 ml), and triphenylphosphine (2.36 g) was added thereto. To the resultant mixture, diethyl azodicarboxylate (1.40 ml) was added under nitrogen steam while ice-cooling, and the mixture was stirred at the same temperature for 40 minutes. Thioacetic acid (0.71 ml) was added to the mixture under ice-cooling, and stirring was continued at room temperature for 3.5 hours. The reaction mixture was diluted with dichloromethane and washed with aqueous sodium bicarbonate solution and aqueous sodium chloride solution in order. The dichloromethane layer was extracted with an aqueous solution of hydrogen chloride (365 mg). The aqueous layer was washed with dichloromethane, neutralized with 1N aqueous sodium hydroxide solution (2.7 ml) and concentrated to remove the solvent. The residue was dissolved in dichloromethane, dried over magnesium sulfate and concentrated. The residue was purified by silica gel column thin layer chromatography to give (2S,4S)-1-methyl-2-methoxycarbonyl-4-acetylthiopyrrolidine.

IR$_{max}^{neat}$ cm$^{-1}$: 1732, 1688, 1438, 1263, 1200.

REFERENCE EXAMPLE 5-5

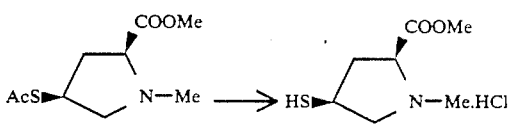

In the same manner as in Reference Example 4-5, there was produced (2S,4S)-1-methyl-2-methoxycarbonyl-4-mercaptopyrrolidine hydrochloride from (2S,4S)-1-methyl-2-methoxycarbonyl-4-acetylthiopyrrolidine (217 mg).

IR$_{max}^{neat}$ cm$^{-1}$: 1748, 1440, 1345, 1250.

REFERENCE EXAMPLE 6-1

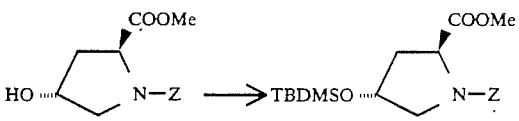

To a solution of trans-1-benzyloxycarbonyl-4-hydroxy-L-proline methyl ester (83.7 g) in dry dimethylformamide (80 ml), imidazole (36.76 g) and t-butyldimethylsilyl chloride (54.26 g) were added, and the resultant mixture was stirred at room temperature for 3 hours. The reaction mixture was diluted with ethyl acetate, washed successively with water, dilute hydrochloric acid and water and dried over magnesium sulfate. Removal of the solvent gave trans-1-benzyloxycarbonyl-4-t-butyldimethylsilyloxy-L-proline methyl ester.

IR$_{max}^{neat}$ cm$^{-1}$: 1750, 1710, 1410, 1350, 1250.

REFERENCE EXAMPLE 6-2

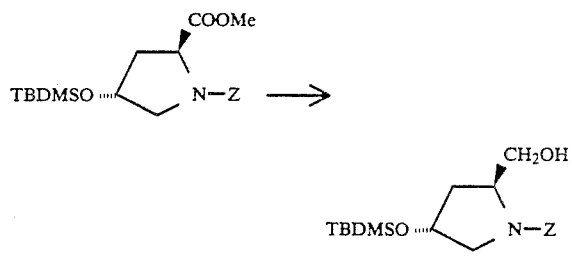

To a suspension of calcium chloride (53.55 g) in dry ethanol (455 ml), sodium borohydride (26.6 g) was added under nitrogen stream while ice-cooling, and the resultant suspension was stirred at the same temperature for 1 hour. A solution of trans-1-benzyloxycarbonyl-4-t-butyldimethylsilyloxy-L-proline methyl ester (68.87 g) in dry ethanol (200 ml) was added thereto while ice-cooling, and the resulting mixture was stirred at the same temperature for 1 hour and at 25° to 30° C. for 2 hours. The reaction mixture was neutralized with 6N hydrochloric acid, poured into water, extracted with ethyl acetate, washed with aqueous sodium chloride solution and dried over magnesium sulfate. Removal of the solvent gave (2S,4R)-1-benzyloxycarbonyl-2-hydroxymethyl-4-t-butyldimethylsilyloxypyrrolidine.

IR$_{max}^{neat}$ cm$^{-1}$: 1700, 1415, 1355, 1250, 1110.

REFERENCE EXAMPLE 6-3

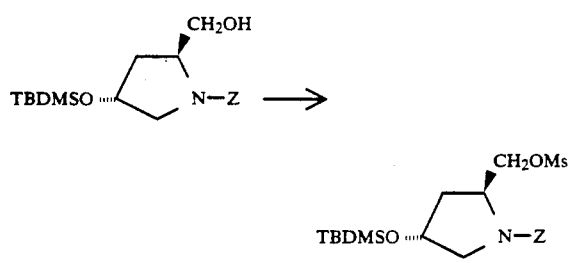

(2S,4R)-1-Benzyloxycarbonyl-2-hydroxymethyl-4-t-butyldimethylsilyloxypyrrolidine (111 g) was dissolved in dry dichloromethane (1100 ml), and triethylamine (36.87 g) was added thereto. After addition of methanesulfonyl chloride (41.81 g) under nitrogen stream while ice-cooling, the resultant mixture was stirred at the same temperature for 30 minutes. The reaction mixture was washed with water, aqueous sodium chloride solution, water, aqueous sodium bicarbonate solution and water in order and dried over magnesium sulfate. Removal of the solvent gave (2S,4R)-1-benzyloxycarbonyl-2-methylsulfonyloxymethyl-4-t-butyldimethylsilyloxypyrrolidine.

IR$_{max}^{neat}$ cm$^{-1}$: 1700, 1410, 1350, 1250, 1172.

REFERENCE EXAMPLE 6-4

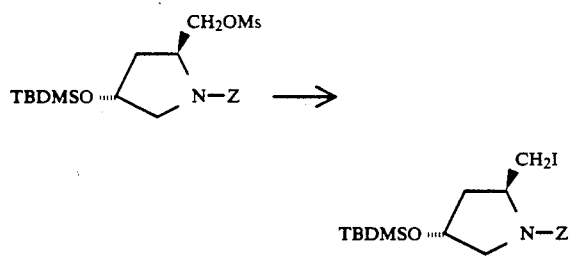

To a solution of (2S,4R)-1-benzyloxycarbonyl-2-methylsulfonyloxymethyl-4-t-butyldimethylsilyloxypyrrolidine (108.5 g) in methylethylketone (1100 ml), potassium iodide (73.5 g) was added, and the resultant mixture was refluxed for 3 hours. The reaction mixture was filtered, and the filtrate was concentrated to remove the solvent. The residue was diluted with ethyl acetate, washed with aqueous sodium chloride solution, aqueous sodium hypochlorite solution and aqueous sodium chloride solution in order and dried over magnesium sulfate. Removal of the solvent gave (2S,4R)-1-benzyloxycarbonyl-2-iodomethyl-4-t-butyldimethylsilyloxypyrrolidine.

IR$_{max}^{neat}$ cm$^{-1}$: 1700, 1403, 1353, 1250, 1103.

REFERENCE EXAMPLE 6-5

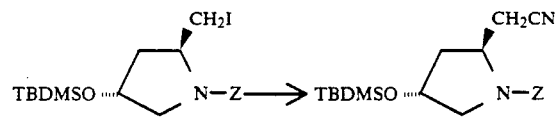

To a solution of (2S,4R)-1-benzyloxycarbonyl-2-iodomethyl-4-t-butyldimethylsilyloxypyrrolidine (110 g) in dry dimethylformamide (300 ml), sodium cyanide (10.29 g) was added, and the resultant mixture was stirred at room temperature for 24 hours. The reaction mixture was diluted with ethyl acetate, washed with aqueous sodium hypochlorite solution and aqueous sodium chloride solution in order and dried over magnesium sulfate. After removal of the solvent, the residue was purified by silica gel column chromatography to give (2R,4R)-1-benzyloxycarbonyl-2-cyanomethyl-4-t-butyldimethylsilyloxypyrrolidine.

IR$_{max}^{neat}$ cm$^{-1}$: 2250, 1695, 1410, 1353, 1110.

REFERENCE EXAMPLE 6-6

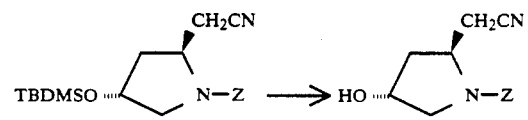

To a solution of (2R,4R)-1-benzyloxycarbonyl-2-cyanomethyl-4-t-butyldimethylsilyloxypyrrolidine (88 g) in methanol (450 ml), 6N hydrochloric acid (45 ml) was added, and the resultant mixture was stirred at room temperature for 1.5 hours. The reaction mixture was diluted with ethyl acetate, washed with aqueous sodium chloride solution and dried over magnesium sulfate. After removal of the solvent, the residue was purified by silica gel column chromatography to give (2R,4R)-1-benzyloxycarbonyl-2-cyanomethyl-4-hydroxypyrrolidine.

IR$_{max}^{neat}$ cm$^{-1}$: 2250, 1705, 1420, 1360, 1118.

REFERENCE EXAMPLE 6-7

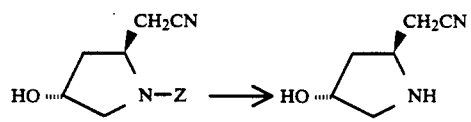

To a solution of (2R,4R)-1-benzyloxycarbonyl-2-cyanomethyl-4-hydroxypyrrolidine (5.94 g) in ethanol (60 ml), 10% palladium-carbon (600 mg) was added, and the resultant mixture was stirred at room temperature for 1.5 hours under an atmospheric pressure of hydrogen, followed by filtration. The filtrate was combined with 10% palladiumcarbon (600 mg) and stirred under the same condition as above. This operation was repeated three times. After removal of the catalyst by filtration, the solvent was removed by distillation to give (2R,4R)-2-cyanomethyl-4-hydroxypyrrolidine.

IR$_{max}^{neat}$ cm$^{-1}$: 2250, 1415, 1358, 1088.

REFERENCE EXAMPLE 6-8

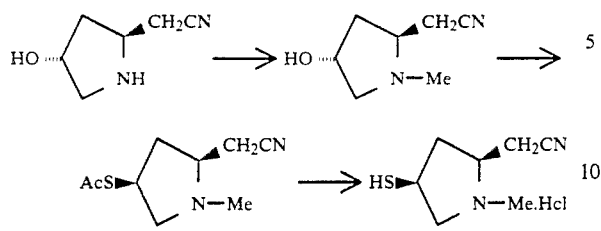

(a) In the same manner as in Reference Example I-4, there was produced (2R,4R)-1-methyl-2-cyanomethyl-4-hydroxypyrrolidine from (2R,4R)-2-cyanomethyl-4-hydroxypyrrolidine (2.87 g).

IR$_{max}^{neat}$ cm$^{-1}$: 2250, 1449, 1418, 1360, 1222.

(b) In the same manner as in Reference Example -5, there was produced (2R,4S)-1-methyl-2-cyanomethyl-4-acetylthiopyrrolidine from (2R,4R)-1-methyl-2-cyanomethyl-4-hydroxypyrrolidine (250 mg).

IR$_{max}^{neat}$ cm$^{-1}$: 2250, 1685, 1450, 1425, 1353, 1267.

(c) In the same manner as in Reference Example -5, there was produced (2R,4S)-1-methyl-2-cyanomethyl-4-mercaptopyrrolidine hydrochloride from (2R,4S)-1-methyl-2-cyanomethyl-4-acetylthiopyrrolidine (128 mg).

IR$_{max}^{neat}$ cm$^{-1}$: 2250, 1460, 1430, 1380, 1307, 1060.

REFERENCE EXAMPLE 7-1

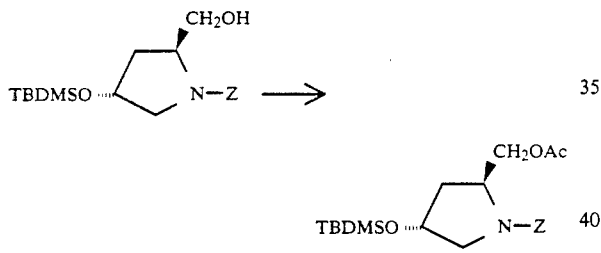

To a solution of (2S,4R)-1-benzyloxycarbonyl-2-hydroxymethyl-4-t-butyldimethylsilyloxypyrrolidine (39.96 in dry pyridine (40 ml), acetic anhydride (40 ml) was added, and the resultant mixture was allowed to stand overnight. The reaction mixture was diluted with ethyl acetate, washed with aqueous sodium chloride solution, dilute hydrochloric acid, aqueous sodium chloride solution, aqueous sodium bicarbonate solution and aqueous sodium chloride solution in order and dried over magnesium sulfate. Removal of the solvent gave (2S,4R)-1-benzyloxycarbonyl-2-acetoxymethyl-4-t-butyldimethylsilyloxypyrrolidine.

IR$_{max}^{neat}$ cm$^{-1}$: 1736, 1703, 1410, 1360, 1245.

REFERENCE EXAMPLE 7-2

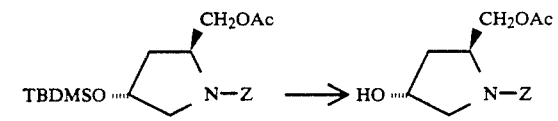

To a solution of (2S,4R)-1-benzyloxycarbonyl-2-acetoxymethyl-4-t-butyldimethylsilyloxypyrrolidine (42.23 g) in dry dichloromethane (422 ml), boron trifluoride etherate (103.54 g) was added at room temperature, and the resultant mixture was stirred at the same temperature for 4 hours. The reaction mixture was washed successively with aqueous sodium bicarbonate solution and water and dried over magnesium sulfate. Removal of the solvent gave (2S,4R)-1-benzyloxycarbonyl-2-acetoxymethyl-4-hydroxypyrrolidine.

IR$_{max}^{neat}$ cm$^{-1}$: 1748, 1690, 1425, 1360, 1235.

REFERENCE EXAMPLE 7-3

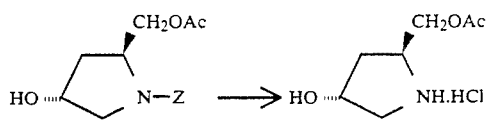

To a solution of (2S,4R)-1-benzyloxycarbonyl-2-acetoxymethyl-4-hydroxypyrrolidine (32.59 g) in ethanol (489 ml), 5% palladium-carbon (4.89 g) and 6N hydrochloric acid (18 ml) were added. The mixture was stirred at room temperature for 1 hour under an atmospheric pressure of hydrogen, followed by removal of the catalyst. Removal of the solvent gave (2S,4R)-2-acetoxymethyl-4-hydroxypyrrolidine hydrochloride.

IR$_{max}^{neat}$ cm$^{-1}$: 1746, 1410, 1375, 1282, 1220.

REFERENCE EXAMPLE 7-4

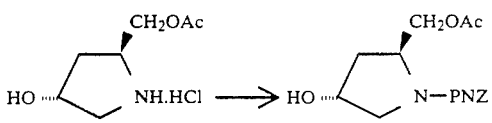

To a solution of (2S,4R)-2-acetoxymethyl-4-hydroxypyrrolidine (22.66 g) in water (100 ml), a solution of S-p-nitrobenzyloxycarbonyl-4,6-dimethyl-2-mercaptopyrimidine (34.45 g) in tetrahydrofuran (453 ml) was added at room temperature, followed by addition of triethylamine (22.54 ml). The resulting mixture was stirred at the same temperature for 30 minutes and diluted with ethyl acetate. The reaction mixture was washed successively with dilute hydrochloric acid and aqueous sodium chloride solution and dried over magnesium sulfate, followed by removal of the solvent. The residue was purified by silica gel column chromatography to give (2S,4R)-1-p-nitrobenzyloxycarbonyl-2-acetoxymethyl4-hydroxypyrrolidine.

IR$_{max}^{neat}$ cm$^{-1}$: 1740, 1700, 1522, 1342, 1235.

REFERENCE EXAMPLE 7-5

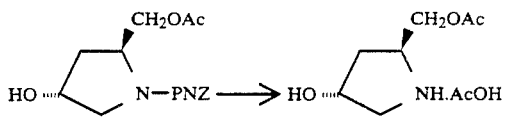

To a solution of (2S,4R)-1-p-nitrobenzyloxycarbonyl-2-acetoxymethyl-4-hydroxypyrrolidine (1.55 g) in ethanol (23 ml), 10% palladium-carbon (233 mg) and acetic acid (330 mg) were added. The mixture was stirred at room temperature for 2 hours under an atmospheric pressure of hydrogen. The reaction mixture was filtered to remove the catalyst. The filtrate was concentrated to remove the solvent. The residue was combined with water, washed with dichloromethane and concentrated to give (2S,4R)-2-acetoxymethyl-4-hydroxypyrrolidine acetate.

IR$_{max}^{Nujol}$ cm$^{-1}$: 1738, 1660, 1558, 1370, 1232.

REFERENCE EXAMPLE 7-6

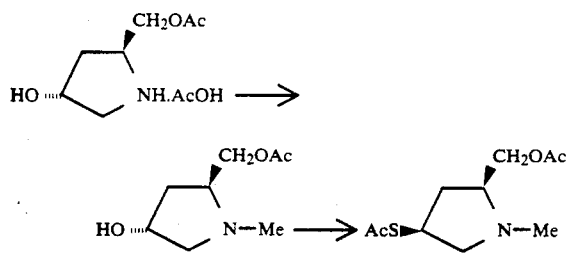

In the same manner as in Reference Examples 1-4 and 1-5, there was produced (2S,4S)-1-methyl-2-acetoxymethyl-4-acetylthiopyrrolidine from (2S,4R)-2-acetoxymethyl-4-hydroxypyrrolidine acetate (870 mg).

$IR_{max}^{neat}$ cm$^{-1}$: 1735, 1683, 1440, 1360, 1218.

REFERENCE EXAMPLE 7-7

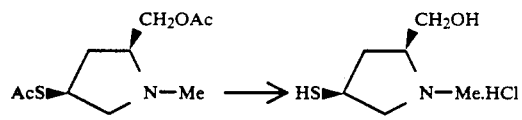

To a solution of (2S,4S)-1-methyl-2-acetoxymethyl-4-acetylthiopyrrolidine (231 mg) in methanol (2.4 ml), a solution of sodium methoxide (130 mg) in methanol (1.4 ml) was added at room temperature under nitrogen stream, and the resultant mixture was stirred at the same temperature for 19 minutes. The reaction mixture was combined with conc. hydrochloric acid (375 mg), followed by removal of the solvent. The residue was dissolved in a mixture of chloroform and methanol (4:1) and dried over magnesium sulfate. Removal of the solvent gave (2S,4S)-1-methyl-2-hydroxymethyl-4-mercaptopyrrolidine hydrochloride.

$IR_{max}^{neat}$ cm$^{-1}$: 1735, 1450, 1380, 1340, 1060.

REFERENCE EXAMPLE 8-1

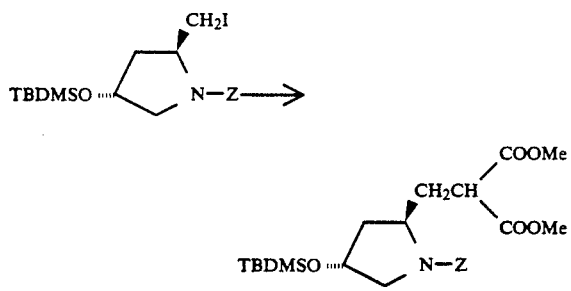

To a solution of (2S,4R)-1-benzyloxycarbonyl-2-iodomethyl-4-t-butyldimethylsilyloxypyrrolidine (100 g) in dry dimethylformamide (500 ml), dimethyl malonate (43.16 ml) and 28% (w/w) methanolic solution of sodium methoxide (60.77 g) were added, and the resultant mixture was stirred at room temperature for 2 days. The reaction mixture was neutralized with 1N hydrochloric acid, diluted with ethyl acetate, washed with water and dried over magnesium sulfate. Removal of the solvent gave (2R,4R)-1-benzyloxycarbonyl-2-(2,2-dimethoxycarbonylethyl)-4-t-butyldimethylsiloxypyrrolidine.

$IR_{max}^{neat}$ cm$^{-1}$: 1735, 1700, 1430, 1403, 1342.

REFERENCE EXAMPLE 8-2

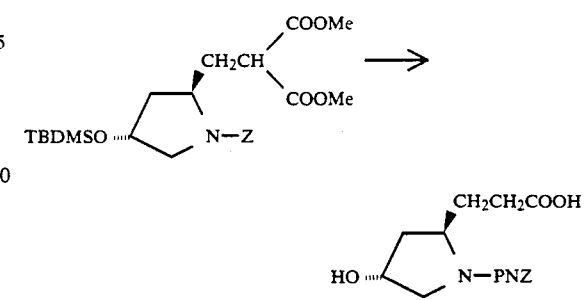

To a solution of (2R,4R)-1-benzyloxycarbonyl-2-(2,2-dimethoxycarbonylethyl)-4-t-butyldimethylsilyloxypyrrolidine (105 g) in acetic acid (266 ml), conc. hydrochloric aid (266 ml) was added, and the resultant mixture was refluxed for 5 hours. After removal of the solvent, the residue was combined with water (266 ml), and triethylamine (124 ml) was added thereto. To the resulting mixture, a solution of S-p-nitrobenzyloxycarbonyl-4,6-dimethyl-2-mercaptopyrimidine (69.86 g) in dimethylformamide (266 ml) was added, followed by stirring at room temperature for 1 hour. Water and aqueous sodium hydroxide solution were added to the reaction mixture, which was washed with ether. The aqueous layer was adjusted to pH 1 with hydrochloric acid and extracted with ethyl acetate. The extract was washed with water, dried over magnesium sulfate and concentrated to give (2R,4R)-1-p-nitrobenzyloxycarbonyl-2-(2-carboxyethyl)-4-hydroxypyrrolidine.

$IR_{max}^{neat}$ cm$^{-1}$: 1710, 1610, 1524, 1435, 1410, 1352.

REFERENCE EXAMPLE 8-3

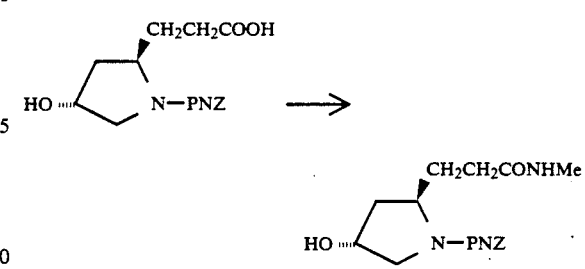

To a solution of (2R,4R)-1-p-nitrobenzyloxycarbonyl-2-(2-carboxyethyl)-4-hydroxypyrrolidine (57.73 g) in dry tetrahydrofuran (500 ml), triethylamine (29.27 ml) was added, and ethyl chloroformate (18.74 ml) was further added thereto at −20° to −25° C. under nitrogen stream. The resulting mixture was stirred at the same temperature for 15 minutes and 30% (w/w) ethanolic solution of methylamine (57.5 g) was added thereto, followed by stirring at the same temperature for 1 hour. The solvent was removed, and the residue was combined with water and ether. The precipitated crystals were collected by filtration to give (2R,4R)-1-p-nitrobenzyloxycarbonyl-2-(2-methylaminocarbonylethyl)-4-hydroxypyrrolidine.

$IR_{max}^{KBr}$ cm$^{-1}$: 1690, 1635, 1525, 1438, 1200.

REFERENCE EXAMPLE 8-4

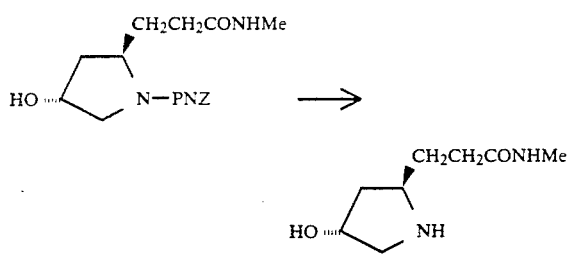

To a solution of (2R,4R)-1-p-nitrobenzyloxycarbonyl-2-(2-methylaminocarbonylethyl)-4-hydroxypyrrolidine (1.52 g) in tetrahydrofuran (15 ml) and ethanol (15 ml), 10 palladium-carbon (228 mg) was added. The mixture was stirred at room temperature for 3.5 hours under an atmospheric pressure of hydrogen. The reaction mixture was filtered to remove the catalyst. The filtrate was concentrated, and the residue was combined with water, washed with dichloromethane and lyophilized to give (2R,4R)-2-(2-methylaminocarbonylethyl)-4-hydroxypyrrolidine.

$IR_{max}^{KBr}$ cm$^{-1}$: 1637, 1560, 1410, 1355, 1155.

REFERENCE EXAMPLE 8-5

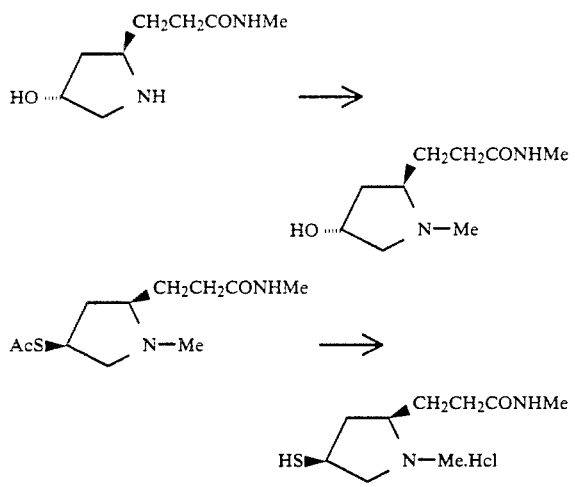

In the same manner as in Reference Examples 1-4, -4 and 4-5, there was produced (2R,4S)-1-methyl-2-(2-methylaminocarbonylethyl)-4-mercaptopyrrolidine hydrochloride from (2R,4R)-2-(2-methylaminocarbonylethyl)-4-hydroxypyrrolidine (670 mg).

$IR_{max}^{neat}$ cm$^{-1}$: 1640, 1543, 1439, 1400, 1255.

REFERENCE EXAMPLE 9-1

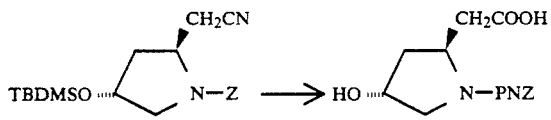

To a solution of (2R,4R)-1-benzyloxycarbonyl-2-cyanomethyl-4-t-butyldimethylsilyloxypyrrolidine (48.4 g) in acetic acid (240 ml), conc. hydrochloric aid (240 ml) was added, and the resultant mixture was refluxed for 4.5 hours. After removal of the solvent, the residue was combined with water (50 ml), and 1N aqueous sodium hydroxide solution (293 ml) was added thereto, followed by removal of the solvent. The residue was dissolved in water (120 ml), and triethylamine (17.88 ml) was added thereto. To the resulting mixture, a solution of S-p-nitrobenzyloxycarbonyl-4,6-dimethyl-2-mercaptopyrimidine (40.32 g) in dimethylformamide (150 ml) was added, followed by stirring at room temperature overnight. The reaction mixture was diluted with water, washed with ether, adjusted to pH 1 with hydrochloric acid and extracted with ethyl acetate. The extract was washed with water, dried over magnesium sulfate and concentrated to give (2S,4R)-1-p-nitrobenzyloxycarbonyl-2-carboxymethyl-4-hydroxypyrrolidine.

$IR_{max}^{Nujol}$ cm$^{-1}$: 1690, 1603, 1517, 1460, 1200, 1116.

REFERENCE EXAMPLE 9-2

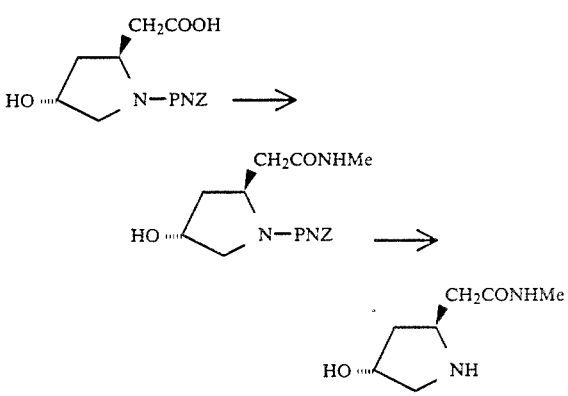

In the same manner as in Reference Examples 8-3 and 8-4, there was produced (2S,4R)-2-methylaminocarbonylmethyl-4-hydroxypyrrolidine from (2S,4R)-1-p-nitrobenzyloxycarbonyl-2-carboxymethyl-4-hydroxypyrrolidine (11 g).

$IR_{max}^{Nujol}$ cm$^{-1}$: 1638, 1555, 1405, 1335, 1088.

REFERENCE EXAMPLE 9-3

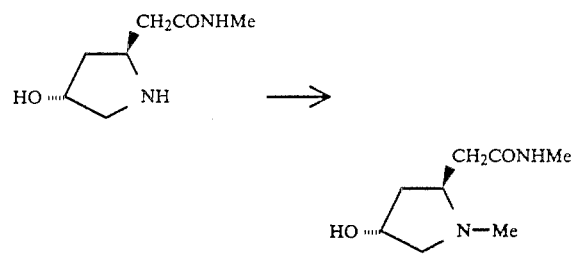

To a solution of (2S,4R)-2-methylaminocarbonyl-4-hydroxypyrrolidine (560 mg) in acetic acid (4.5 ml) and water (2.5 ml), 35% (w/w) aqueous formaldehyde solution (0.39 g) and platinum oxide (30 mg) were added. Hydrogen gas was introduced therein at room temperature for 6 hours under an ordinary hydrogen pressure. The reaction mixture was filtered to eliminate the catalyst. The filtrate was concentrated to remove the solvent. The residue was dissolved in dichloromethane, dried over magnesium sulfate and potassium carbonate and concentrated to remove the solvent. The residue was dissolved in formic acid (1.73 ml), 35% (w/w) aqueous formaldehyde solution (1.52 ml) was added thereto, and the resulting mixture was refluxed for 4.5 hours, followed by removal of the solvent. The residue was dissolved in a mixture of chloroform and methanol (4 : 1) and dried over potassium carbonate. After removal of the solvent, the residue was purified by silica gel column chromatography to give (2S,4R)-1-methyl-2-methylaminocarbonylmethyl-4-hydroxypyrrolidine.

IR$_{max}^{neat}$ cm$^{-1}$: 1638, 1555, 1445, 1405, 1210.

REFERENCE EXAMPLE 9-4

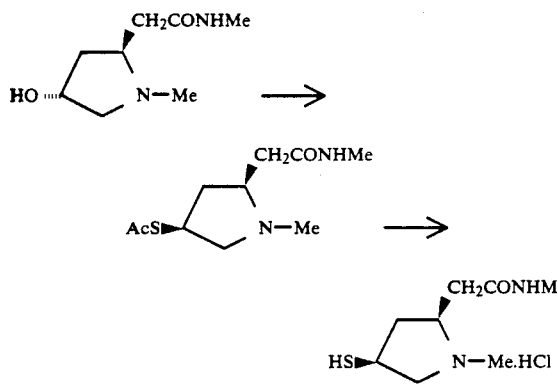

In the same manner as in Reference Examples 4-4 and 4-5, there was produced (2R,4R)-1-methyl-2-methylaminocarbonylmethyl-4-mercaptopyrrolidine hydrochloride from (2S,4R)-1-methyl-2-methylaminocarbonylmethyl-4-hydroxypyrrolidine (190 mg).

IR$_{max}^{neat}$ cm$^{-1}$: 1643, 1555, 1445, 1405, 1025.

What is claimed is:

1. A beta-lactam compound of the formula:

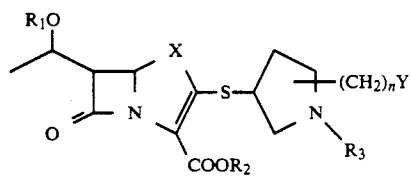

wherein
 $R_1$ is a hydrogen atom or a protective group for hydroxyl;
 $R_2$ is a hydrogen atom or a protective group for carboxyl;
 $R_3$ is a $C_1$–$C_3$ loweralkyl group;
 X is a methylene group optionally substituted by a $C_1$–$C_3$ loweralkyl group;
 Y is —CON($R_4$)($R_5$), $C_1$–$C_3$ loweralkoxy carbonyl, —CN, or —OH;
 n is 0 to 4;
 $R_4$ and $R_5$, same or different, are hydrogen, or $C_1$–$C_3$ loweralkyl, or, they are combined together to form a $C_2$–$C_6$ alkylene group; or a pharmaceutically acceptable salt thereof.

2. The beta-lactam compound of claim 1, wherein X is a methylene group optionally substituted by a methyl group, or a pharmaceutically acceptable salt thereof.

3. The beta-lactam compound of claim 1, wherein $R_3$ is a methyl group, or a pharmaceutically acceptable salt thereof.

4. The beta-lactam compound of claim 1, which has a (4R, 5S, 6S, 8R) configuration.

5. The beta-lactam compound of claim 1, which has a (5R, 6S, 8R) configuration.

6. The beta-lactam compound of claim 1, which is (4R, 5S, 6S, 8R, 2'S, 4'S)-3-[(1-methyl-2-dimethylaminocarbonylpyrrolidin) -4-ylthio]-4-methyl-6-(1-hydroxyethyl)-1-azabicyclo[3.2.0.]-2-2-en-7-one-2-carboxylic acid, or a pharmaceutically acceptable salt thereof.

7. The beta-lactam compound of claim 1, which is (4R, 5S, 6S, 8R, 2'R, 4'R)-3-[(1-methyl-2-methylaminocarbonylmethylpyrrolidin-4-ylthio]-4-methyl-6-(1-hydroxyethyl)-1-azabicyclo [3.2.0]hept-2-en-7-one-2-carboxylic acid, or a pharmaceutically acceptable salt thereof.

8. The beta-lactam compound of claim 1, which is (4R, 5S, 6S, 8R, 2'S, 4'S)-3-[(1-methyl-2-hydroxymethylpyrrolidin)-4-ylthio]-4-methyl-6-(1-hydroxyethyl)-1-azabicyclo[3.2.0]hept-2-en-7-one-2-carboxylic acid, or a pharmaceutically acceptable salt thereof.

9. The beta-lactam compound of claim 1, which is (4R, 5S, 6S, 8R, 2'R, 4'S)-3-[(1-methyl-2-(2-(methylaminocarbonyl)ethyl) pyrrolidin)-4-ylthio]-4-methyl-6-(1-hydroxyethyl)-1-azabicyclo [3.2.0]hept-2-en-7-one-2-carboxylic acid, or a pharmaceutically acceptable salt thereof.

10. The beta-lactam compound of claim 1, which is (4R, 5S, 6S, 8R, 2'S, 4'S)-3-[(1-methyl-2-methylaminocarbonylpyrrolidin)-4-ylthio]-4-methyl-6-(1-hydroxyethyl)-1-azabicyclo[3.2.0]hept-2-en -7-one-2-carboxylic acid, or a pharmaceutically acceptable salt thereof.

11. The beta-lactam compound of claim 1, which is (4R, 5S, 6S, 8R, 2'S, 4'S)-3-[(2-aminocarbonyl-1-methylpyrrolidin)-b 4-ylthio]-4-methyl-6-(hydroxyethyl)-1-azabicyclo[3.2.0]hept-2-en-7-one-2 -carboxylic acid, or a pharmaceutically acceptable salt thereof.

12. The beta-lactam compound of claim 1, which is (4R, 5S, 6S, 8R, 2'S, 4'S)-3-[(1-methyl-2-(1-pyrrolidincarbonyl)pyrrolidin) -4-yl-thio]-4-methyl-6-(hydroxyethyl)-1-azabicyclo[3.2.0]hept-2-en -7-one-2-carboxylic acid, or a pharmaceutically acceptable salt thereof.

13. A pharmaceutical composition for treatment of a microbial infection which comprises as an active ingredient a pharmaceutically effective antimicrobial amount of a compound of formula (I):

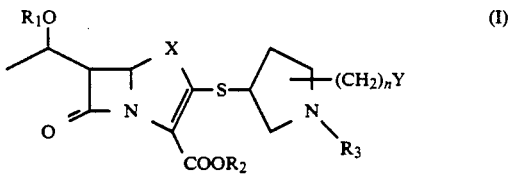

wherein
 $R_1$ is a hydrogen atom or a protective group for hydroxyl;
 $R_2$ is a hydrogen atom or a protective group for carboxyl;
 $R_3$ is a $C_1$–$C_3$ loweralkyl group;
 X is a methylene group optionally substituted by a $C_1$–$C_3$ loweralkyl group;
 Y is —CON($R_4$)($R_5$), $C_1$–$C_3$ loweralkoxyl carbonyl, —CN, or —OH;
 n is 0 to 4;
 $R_4$ and $R_5$, same or different, are hydrogen, or $C_1$–$C_3$ loweralkyl, or, they are combined together to form a $C_2$–$C_6$ alkylene group; and an acceptable inert carrier or diluent therefor.

14. The pharmaceutical composition of claim 13, wherein said Formula I compound is (4R, 5S, 6S, 8R, 2′S, 4′S)-3-[(1-methyl -2-dimethylaminocarbonylpyrrolidin)-4-ylthio]-4-methyl-6-(1-hydroxyethyl)-1-azabicyclo[3.2.0]hept-2-en-7-one-2-carboxylic acid, or a pharmaceutically acceptable salt thereof.

15. The pharmaceutical composition of claim 13, wherein said Formula I compound is (4R, 5S, 6S, 8R, 2′R, 4′R)-3-[(1-methyl-2-methylaminocarbonylmethylpyrrolidin)-4-ylthio]-4-methyl-6-(1-hydroxyethyl)-1-azabicyclo[3.2.0]hept-2-en-7-one-2-carboxylic acid, or a pharmaceutically acceptable salt thereof.

16. The pharmaceutical composition of claim 13, wherein said Formula I compound is (4R, 5S, 6S, 8R, 2′S, 4′S)-3-[(1-methyl-2-hydroxymethylpyrrolidin) -4-ylthio]-4-methyl-6-(1-hydroxyethyl)-1-azabicyclo[3.2.0]-hept-2-en-7-one-2-carboxylic acid, or a pharmaceutically acceptable salt thereof.

17. The pharmaceutical composition of claim 13, wherein said Formula I compound is (4R, 5S, 6S, 8R, 2′R, 4′S)-3-[(1-methyl-2-(2-(methylaminocarbonyl)ethyl) pyrrolidin)-4-ylthio]-4-methyl-6-(1-hydroxyethyl) -1-azabicyclo[3.2.0]hept-2-en-7-one-2-carboxylic acid, or a pharmaceutically acceptable salt thereof.

18. The pharmaceutical composition of claim 13, wherein said Formula I compound is (4R, 5S, 6S, 8R, 2′S, 4′S)-3-[(1-methyl-2-methylaminocarbonylcarbonylpyrrolidin)-4-ylthio]-4-methyl-6-(1-hydroxyethyl)-1-azabicyclo[3.2.0]hept-2-en-7-one-2-carboxylic acid, or a pharmaceutically acceptable salt thereof.

19. The pharmaceutical composition of claim 13, wherein said Formula I compound is (4R, 5S, 6S, 8R, 2′S, 4′S)-3-[(2-aminocarbonyl-1-methylpyrrolidin) -4-ylthio]-4-methyl-6-(hydroxyethyl)-1-azabicyclo[3.2.0-]hept-2-en -7-one-2-carboxylic acid, or a pharmaceutically acceptable salt thereof.

20. A method of treating a microbial infection, which comprises applying an antimicrobial effective amount of the compound of claim 1 to said microbial infection.

21. The method according to claim 20, wherein said microbial infection is caused by gram-positive or gram-negative bacteria.

22. The method according to claim 20, wherein said microbial infection is caused by a beta-lactamase-producing bacteria.

23. The method according to claim 21, wherein said infection is caused by bacteria selected from the group consisting of *Staphylococcus, aurens, Staphylococcus epidermides, Streptococcus pyrogens, Streptococcus faecalis, Escherichia coli, Proteus millabilis, Seratia malcescens,* and *Pseudomonas aeruginosa.*

24. The beta-lactam compound of claim 1, which is (4R, 5S, 6S, 8R, 2′S, 4′S)-3-[(1-methyl-2-methoxycarbonylpyrrolidin)-4-ylthio]-4-methyl-6-(1-hydroxyethyl)-1-azabicyclo[3.2.0]hept-2-en-7-one-2-carboxylic acid, or a pharmaceutically acceptable salt thereof.

25. The beta-lactam compound of claim 1, which is (4R, 5S, 6S, 8R, 2′R, 4′S)-3-[(1-methyl-2-cyanomethylpyrrolidin) -4-ylthio]-4-methyl-6-(1-hydroxyethyl)-1-azabicyclo[3.2.0]hept-2-en-7-one-2-carboxylic acid, or a pharmaceutically acceptable salt thereof.

26. The pharmaceutical composition of claim 13, wherein the Formula I compound is (4R, 5S, 6S, 8R, 2′S, 4′S)-3-[(1-methyl-2-methoxycarbonylpyrrolidin)-4-ylthio]-4-methyl-6-(1-hydroxyethyl)-1-azabicyclo[3.2.0-]hept-2-en-7-one-2-carboxylic acid, or a pharmaceutically acceptable salt thereof.

27. The pharmaceutically composition of claim 13, wherein the Formula I compound is (4R, 5S, 6S, 8R, 2′R, 4′S)-3-[1-methyl-2-cyanomethylpyrrolidin)-4-ylthio]-4-methyl-6-(1-hydroxyethyl)-1-azabicyclo[3.2.0-]hept-2-en-7-one-2-carboxylic acid, or a pharmaceutically acceptable salt thereof.

28. The pharmaceutically composition of claim 13, wherein the Formula I compound is (4R, 5S,6S, 8R, 2′S, 4′S)-3-[(1-methyl-2-(1-pyrrolidincarbonyl)pyrrolidin)-4-yl-thio]-4-methyl-6-(hydroxyethyl)-1-azabicyclo[3.2.0]hept-2-en -7-one-2-carboxylic acid, or a pharmaceutically acceptable salt thereof.

* * * * *